(12) United States Patent
Shimizu et al.

(10) Patent No.: US 10,435,411 B2
(45) Date of Patent: Oct. 8, 2019

(54) OXIME GROUP-CONTAINING QUINOLINE COMPOUND, N-OXIDE THEREOF OR SALT THEREOF, AGRICULTURAL AND HORTICULTURAL INSECTICIDE COMPRISING THE COMPOUND, AND METHOD FOR USING THE INSECTICIDE

(71) Applicant: Nihon Nohyaku Co., Ltd., Tokyo (JP)

(72) Inventors: Naoto Shimizu, Osaka (JP); Ikki Yonemura, Osaka (JP); Yusuke Sano, Osaka (JP); Akiyuki Suwa, Osaka (JP); Shunpei Fujie, Osaka (JP)

(73) Assignee: Nihon Nohyaku Co., Ltd., Tokyo (JP)

( * ) Notice: Subject to any disclaimer, the term of this patent is extended or adjusted under 35 U.S.C. 154(b) by 0 days.

(21) Appl. No.: 16/346,047

(22) PCT Filed: Oct. 31, 2017

(86) PCT No.: PCT/JP2017/039323
§ 371 (c)(1),
(2) Date: Apr. 29, 2019

(87) PCT Pub. No.: WO2018/084142
PCT Pub. Date: May 11, 2018

(65) Prior Publication Data
US 2019/0248796 A1   Aug. 15, 2019

(30) Foreign Application Priority Data

Nov. 1, 2016 (JP) .................................. 2016-214099
Mar. 24, 2017 (JP) .................................. 2017-060207

(51) Int. Cl.
| | | |
|---|---|---|
| C07D 487/04 | (2006.01) |
| C07D 401/04 | (2006.01) |
| C07D 413/04 | (2006.01) |
| C07D 471/04 | (2006.01) |
| A61P 33/14 | (2006.01) |
| A01N 43/52 | (2006.01) |
| A01N 43/76 | (2006.01) |
| A01N 43/90 | (2006.01) |
| A61K 31/4709 | (2006.01) |
| A61K 31/5025 | (2006.01) |

(52) U.S. Cl.
CPC .......... *C07D 487/04* (2013.01); *A01N 43/52* (2013.01); *A01N 43/76* (2013.01); *A01N 43/90* (2013.01); *A61K 31/4709* (2013.01); *A61K 31/5025* (2013.01); *A61P 33/14* (2018.01); *C07D 401/04* (2013.01); *C07D 413/04* (2013.01); *C07D 471/04* (2013.01)

(58) Field of Classification Search
CPC .. C07D 487/04; C07D 401/04; C07D 413/04; C07D 471/04; A61P 33/14; A01N 43/52; A01N 43/76; A01N 43/90; A61K 31/4709; A61K 31/5025
See application file for complete search history.

(56) References Cited

U.S. PATENT DOCUMENTS

| | | |
|---|---|---|
| 5,055,471 A | 10/1991 | De Fraine et al. |
| 5,371,084 A | 12/1994 | De Fraine et al. |
| 5,432,197 A | 7/1995 | De Fraine et al. |
| 5,631,253 A | 5/1997 | De Fraine et al. |
| 5,763,640 A | 6/1998 | De Fraine et al. |
| 10,266,552 B2 * | 4/2019 | Yonennura ............. A01N 43/52 |
| 2011/0039843 A1 | 2/2011 | Iwakoshi et al. |
| 2012/0015975 A1 | 1/2012 | Takahashi et al. |
| 2012/0108586 A1 | 5/2012 | Iwakoshi et al. |
| 2012/0178779 A1 | 7/2012 | Takahashi et al. |

(Continued)

FOREIGN PATENT DOCUMENTS

| | | |
|---|---|---|
| EP | 2 955 179 A1 | 12/2015 |
| EP | 3 372 595 A1 | 9/2018 |

(Continued)

OTHER PUBLICATIONS

International Preliminary Report on Patentability for PCT/JP2017/039323 dated May 7, 2019.
International Search Report for PCT/JP2017/039323.

*Primary Examiner* — Timothy R Rozof
(74) *Attorney, Agent, or Firm* — Knobbe Martens Olson & Bear LLP

(57) ABSTRACT

In crop production in the fields of agriculture, horticulture and the like, the damage caused by insect pests etc. is still immense, and insect pests resistant to existing insecticides have emerged. The present invention has been made in view of such circumstances, and an object of the present invention is to develop and provide a novel agricultural and horticultural insecticide. The present invention provides an oxime group-containing quinoline compound represented by the general formula (1):

[Chem. 1]

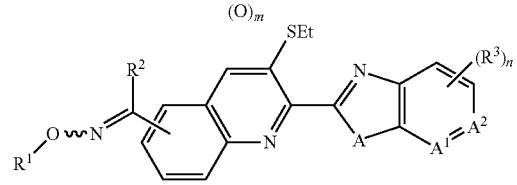

(1)

(wherein $R^1$ is a haloalkyl group, $R^2$ is a hydrogen atom or an alkyl group, $R^3$ is a haloalkyl group or an alkylthio alkyl group, A is an N-methyl group, $A^1$ is a nitrogen atom, $A^2$ is CH, m is 2, and n is 1), or a salt thereof; an agricultural and horticultural insecticide comprising the compound or a salt thereof as an active ingredient; and a method for using the insecticide.

6 Claims, No Drawings

(56) References Cited

U.S. PATENT DOCUMENTS

| | | |
|---|---|---|
| 2012/0196891 A1 | 8/2012 | Iwakoshi |
| 2012/0245167 A1 | 9/2012 | Iwakoshi et al. |
| 2013/0190271 A1 | 7/2013 | Iwakoshi et al. |
| 2013/0252981 A1 | 9/2013 | Takahashi et al. |
| 2014/0018373 A1 | 1/2014 | Takyo et al. |
| 2014/0194290 A1 | 7/2014 | Takahashi et al. |
| 2014/0364444 A1 | 12/2014 | Takyo et al. |
| 2015/0197532 A1 | 7/2015 | Takahashi et al. |
| 2016/0009715 A1 | 1/2016 | Takahashi et al. |
| 2016/0159743 A1 | 6/2016 | Takahashi et al. |
| 2017/0073342 A1 | 3/2017 | Fischer et al. |
| 2017/0349581 A1 | 12/2017 | Jung et al. |
| 2018/0002347 A1 | 1/2018 | Yonemura et al. |
| 2019/0045786 A1 | 2/2019 | Matsuo et al. |

FOREIGN PATENT DOCUMENTS

| | | |
|---|---|---|
| EP | 3 421 475 A1 | 1/2019 |
| JP | 2-188565 A | 7/1990 |
| JP | 2009-280574 A | 12/2009 |
| JP | 2010-275301 A | 12/2010 |
| JP | 2011-79774 A | 4/2011 |
| JP | 2012-131780 A | 7/2012 |
| WO | WO 2012/086848 A1 | 6/2012 |
| WO | WO 2013/018928 A1 | 2/2013 |
| WO | WO 2014/123206 A1 | 8/2014 |
| WO | WO 2015/121136 A1 | 8/2015 |
| WO | WO 2016/039444 A1 | 3/2016 |
| WO | WO 2016/091731 A1 | 6/2016 |
| WO | WO 2016/121997 A1 | 8/2016 |
| WO | WO 2017/065183 A1 | 4/2017 |
| WO | WO 2017/146220 A2 | 8/2017 |
| WO | WO 2017/146221 A1 | 8/2017 |
| WO | WO 2017/146226 A1 | 8/2017 |

* cited by examiner

OXIME GROUP-CONTAINING QUINOLINE COMPOUND, N-OXIDE THEREOF OR SALT THEREOF, AGRICULTURAL AND HORTICULTURAL INSECTICIDE COMPRISING THE COMPOUND, AND METHOD FOR USING THE INSECTICIDE

CROSS REFERENCE TO RELATED APPLICATIONS

This application is a U.S. National Phase Application of PCT International Application Number PCT/JP2017/039323, filed on Oct. 31, 2017, designating the United States of America and published in the Japanese language, which is an International Application of and claims the benefit of priority to Japanese Patent Application No. 2016-214099, filed on Nov. 1, 2016, and Japanese Patent Application No. 2017-060207, filed on Mar. 24, 2017. The disclosures of the above-referenced applications are hereby expressly incorporated by reference in their entireties.

TECHNICAL FIELD

The present invention relates to an agricultural and horticultural insecticide comprising an oxime group-containing quinoline compound, an N-oxide thereof or a salt thereof as an active ingredient, and a method for using the insecticide.

BACKGROUND ART

Various compounds have been examined for their potential as agricultural and horticultural insecticides, and among them, certain kinds of condensed heterocyclic compounds have been reported to be useful as insecticides (for example, see Patent Literature 1 to 8). The literature, however, does not disclose any oxime group-containing quinoline compound.

CITATION LIST

Patent Literature

Patent Literature 1: JP-A 2009-280574
Patent Literature 2: JP-A 2010-275301
Patent Literature 3: JP-A 2011-79774
Patent Literature 4: JP-A 2012-131780
Patent Literature 5: WO 2012/086848
Patent Literature 6: WO 2013/018928
Patent literature 7: WO 2015/121136
Patent literature 8: WO 2016/091731

SUMMARY OF INVENTION

Technical Problem

In crop production in the fields of agriculture, horticulture and the like, the damage caused by insect pests etc. is still immense, and insect pests resistant to existing insecticides have emerged. Under such circumstances, the development of novel agricultural and horticultural insecticides is desired.

Solution to Problem

The present inventors conducted extensive research to solve the above-described problems. As a result, the present inventors found that an oxime group-containing quinoline compound represented by the general formula (1), an N-oxide thereof and a salt thereof are highly effective for the control of agricultural and horticultural pests, for example, when used for foliar application and/or soil treatment. Based on this finding, the present inventors completed the present invention.

That is, the present invention includes the following.

[1] An oxime group-containing quinoline compound represented by the general formula (1):

[Chem. 1]

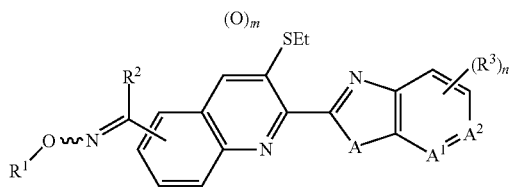

(1)

{wherein
R$^1$ represents
(a1) a hydrogen atom;
(a2) a ($C_1$-$C_6$) alkyl group;
(a3) a ($C_2$-$C_6$) alkenyl group;
(a4) a ($C_2$-$C_6$) alkynyl group;
(a5) a ($C_3$-$C_6$) cycloalkyl group;
(a6) a ($C_3$-$C_6$) cycloalkyl ($C_1$-$C_6$) alkyl group;
(a7) a ($C_1$-$C_6$) alkoxy ($C_1$-$C_6$) alkyl group;
(a8) a halo ($C_1$-$C_6$) alkyl group;
(a9) a halo ($C_2$-$C_6$) alkenyl group;
(a10) a halo ($C_2$-$C_6$) alkynyl group;
(a11) a ($C_1$-$C_6$) alkylthio ($C_1$-$C_6$) alkyl group;
(a12) a phenyl ($C_1$-$C_6$) alkyl group;
(a13) a phenyl ($C_1$-$C_6$) alkyl group having, on the ring, 1 to 5 substituting groups which may be the same or different and are selected from (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group and (o) a halo ($C_1$-$C_6$) alkylsulfonyl group;
(a14) a ($C_1$-$C_6$) alkylsulfinyl ($C_1$-$C_6$) alkyl group;
(a15) a ($C_1$-$C_6$) alkylsulfonyl ($C_1$-$C_6$) alkyl group;
(a16) a ($C_1$-$C_6$) alkylcarbonyl group;
(a17) a ($C_1$-$C_6$) alkoxycarbonyl group;
(a18) a halo ($C_1$-$C_6$) alkylthio ($C_1$-$C_6$) alkyl group; or
(a19) a ($C_1$-$C_6$) alkyl (N=CN=)S($C_1$-$C_6$) alkyl group,
R$^2$ represents
(b1) a hydrogen atom;
(b2) a ($C_1$-$C_6$) alkyl group;
(b3) a cyano group; or
(b4) a ($C_3$-$C_6$) cycloalkyl group,
R$^3$ represents
(c1) a halogen atom;
(c2) a cyano group;
(c3) a nitro group;
(c4) a ($C_1$-$C_6$) alkyl group;
(c5) a ($C_1$-$C_6$) alkoxy group;
(c6) a ($C_2$-$C_6$) alkenyloxy group;
(c7) a ($C_2$-$C_6$) alkynyloxy group;
(c8) a halo ($C_1$-$C_6$) alkyl group;

(c9) a halo $(C_1-C_6)$ alkoxy group;
(c10) a halo $(C_2-C_6)$ alkenyloxy group;
(c11) a halo $(C_2-C_6)$ alkynyloxy group;
(c12) a $(C_1-C_6)$ alkylthio group;
(c13) a $(C_1-C_6)$ alkylsulfinyl group;
(c14) a $(C_1-C_6)$ alkylsulfonyl group;
(c15) a halo $(C_1-C_6)$ alkylthio group;
(c16) a halo $(C_1-C_6)$ alkylsulfinyl group; or
(c17) a halo $(C_1-C_6)$ alkylsulfonyl group, A represents an oxygen atom or N—$R^4$ (wherein $R^4$ represents a hydrogen atom or a $(C_1-C_6)$ alkyl group), $A^1$ and $A^2$ may be the same or different, and each represent CH, a nitrogen atom or an N-oxide, m represents 0, 1 or 2, and n represents 0, 1 or 2}, or a salt thereof.

[2] The oxime group-containing quinoline compound or the salt according to the above [1], wherein $R^1$ represents
(a1) a hydrogen atom;
(a2) a $(C_1-C_6)$ alkyl group;
(a6) a $(C_3-C_6)$ cycloalkyl $(C_1-C_6)$ alkyl group;
(a7) a $(C_1-C_6)$ alkoxy $(C_1-C_6)$ alkyl group;
(a8) a halo $(C_1-C_6)$ alkyl group;
(a11) a $(C_1-C_6)$ alkylthio $(C_1-C_6)$ alkyl group;
(a14) a $(C_1-C_6)$ alkylsulfinyl $(C_1-C_6)$ alkyl group;
(a15) a $(C_1-C_6)$ alkylsulfonyl $(C_1-C_6)$ alkyl group;
(a16) a $(C_1-C_6)$ alkylcarbonyl group;
(a17) a $(C_1-C_6)$ alkoxycarbonyl group;
(a18) a halo $(C_1-C_6)$ alkylthio $(C_1-C_6)$ alkyl group; or
(a19) a $(C_1-C_6)$ alkyl (N≡CN═)S$(C_1-C_6)$ alkyl group, $R^2$ represents
(b1) a hydrogen atom;
(b2) a $(C_1-C_6)$ alkyl group; or
(b3) a cyano group, $R^3$ represents
(c8) a halo $(C_1-C_6)$ alkyl group;
(c15) a halo $(C_1-C_6)$ alkylthio group; or
(c17) a halo $(C_1-C_6)$ alkylsulfonyl group, A represents an oxygen atom or N—$R^4$ (wherein $R^4$ represents a $(C_1-C_6)$ alkyl group), $A^1$ and $A^2$ each represent CH or a nitrogen atom, m represents 2, and n represents 1.

[3] The oxime group-containing quinoline compound or the salt according to the above [1], wherein $R^1$ represents
(a1) a hydrogen atom;
(a2) a $(C_1-C_6)$ alkyl group;
(a6) a $(C_3-C_6)$ cycloalkyl $(C_1-C_6)$ alkyl group;
(a7) a $(C_1-C_6)$ alkoxy $(C_1-C_6)$ alkyl group;
(a8) a halo $(C_1-C_6)$ alkyl group;
(a11) a $(C_1-C_6)$ alkylthio $(C_1-C_6)$ alkyl group;
(a14) a $(C_1-C_6)$ alkylsulfinyl $(C_1-C_6)$ alkyl group;
(a15) a $(C_1-C_6)$ alkylsulfonyl $(C_1-C_6)$ alkyl group;
(a16) a $(C_1-C_6)$ alkylcarbonyl group;
(a17) a $(C_1-C_6)$ alkoxycarbonyl group;
(a18) a halo $(C_1-C_6)$ alkylthio $(C_1-C_6)$ alkyl group; or
(a19) a $(C_1-C_6)$ alkyl (N≡CN═)S$(C_1-C_6)$ alkyl group, $R^2$ represents
(b1) a hydrogen atom; or
(b2) a $(C_1-C_6)$ alkyl group, $R^3$ represents
(c8) a halo $(C_1-C_6)$ alkyl group;
(c15) a halo $(C_1-C_6)$ alkylthio group; or
(c17) a halo $(C_1-C_6)$ alkylsulfonyl group, A represents an oxygen atom or N—$R^4$ (wherein $R^4$ represents a $(C_1-C_6)$ alkyl group), $A^1$ and $A^2$ may be the same or different, and each represent CH or a nitrogen atom, m represents 2, and n represents 1.

[4] An agricultural and horticultural insecticide comprising the oxime group-containing quinoline compound or the salt according to any of the above [1] to [3] as an active ingredient.

[5] A method for using an agricultural and horticultural insecticide, comprising treating plants or soil with an effective amount of the oxime group-containing quinoline compound or the salt according to any of the above [1] to [3].

[6] An animal ectoparasite control agent comprising the oxime group-containing quinoline compound or the salt according to any of the above [1] to [3] as an active ingredient.

Advantageous Effects of Invention

The oxime group-containing quinoline compound of the present invention or a salt thereof is not only highly effective as an agricultural and horticultural insecticide but also effective against parasites of non-human animals including pets such as dogs and cats and domestic animals such as cattle and sheep.

DESCRIPTION OF EMBODIMENTS

In the definitions of the general formula (1) representing the oxime group-containing quinoline compound of the present invention or a salt thereof, "halo" refers to a "halogen atom" and represents a chlorine atom, a bromine atom, an iodine atom or a fluorine atom.

The "$(C_1-C_6)$ alkyl group" refers to a straight-chain or branched-chain alkyl group of 1 to 6 carbon atoms, for example, a methyl group, an ethyl group, a n-propyl group, an isopropyl group, a n-butyl group, an isobutyl group, a sec-butyl group, a tert-butyl group, a n-pentyl group, an isopentyl group, a tert-pentyl group, a neopentyl group, a 2,3-dimethylpropyl group, an 1-ethylpropyl group, a 1-methylbutyl group, a 2-methylbutyl group, a n-hexyl group, an isohexyl group, a 2-hexyl group, a 3-hexyl group, a 2-methylpentyl group, a 3-methylpentyl group, a 1,1,2-trimethyl propyl group, a 3,3-dimethylbutyl group or the like.

The "$(C_2-C_6)$ alkenyl group" refers to a straight-chain or branched-chain alkenyl group of 2 to 6 carbon atoms, for example, a propenyl group, a butenyl group, a pentenyl group, a hexenyl group or the like. The "$(C_2-C_6)$ alkynyl group" refers to a straight-chain or branched-chain alkynyl group of 2 to 6 carbon atoms, for example, a propynyl group, a butynyl group, a pentynyl group, a hexynyl group or the like.

The "$(C_3-C_6)$ cycloalkyl group" refers to a cyclic alkyl group of 3 to 6 carbon atoms, for example, a cyclopropyl group, a cyclobutyl group, a cyclopentyl group, a cyclohexyl group or the like. The "$(C_1-C_6)$ alkoxy group" refers to a straight-chain or branched-chain alkoxy group of 1 to 6 carbon atoms, for example, a methoxy group, an ethoxy group, a n-propoxy group, an isopropoxy group, a n-butoxy group, a sec-butoxy group, a tert-butoxy group, a n-pentyloxy group, an isopentyloxy group, a tert-pentyloxy group, a neopentyloxy group, a 2,3-dimethylpropyloxy group, an 1-ethylpropyloxy group, a 1-methylbutyloxy group, a n-hexyloxy group, an isohexyloxy group, a 1,1,2-trimethylpropyloxy group or the like. The "(C$_2$-C$_6$) alkenyloxy group" refers to a straight-chain or branched-chain alkenyloxy group of 2 to 6 carbon atoms, for example, a propenyloxy group, a butenyloxy group, a pentenyloxy group, a hexenyloxy group or the like. The "(C$_2$-C$_6$) alkynyloxy group" refers to a straight-chain or branched-chain alkynyloxy group of 2 to 6 carbon atoms, for example, a propynyloxy group, a butynyloxy group, a pentynyloxy group, a hexynyloxy group or the like.

The "(C$_1$-C$_6$) alkylthio group" refers to a straight-chain or branched-chain alkylthio group of 1 to 6 carbon atoms, for example, a methylthio group, an ethylthio group, a n-propylthio group, an isopropylthio group, a n-butylthio group, a sec-butylthio group, a tert-butylthio group, a n-pentylthio group, an isopentylthio group, a tert-pentylthio group, a neopentylthio group, a 2,3-dimethylpropylthio group, an 1-ethylpropylthio group, a 1-methylbutylthio group, a n-hexylthio group, an isohexylthio group, a 1,1,2-trimethylpropylthio group or the like. The "(C$_1$-C$_6$) alkylsulfinyl group" refers to a straight-chain or branched-chain alkylsulfinyl group of 1 to 6 carbon atoms, for example, a methylsulfinyl group, an ethylsulfinyl group, a n-propylsulfinyl group, an isopropylsulfinyl group, a n-butylsulfinyl group, a sec-butylsulfinyl group, a tert-butylsulfinyl group, a n-pentylsulfinyl group, an isopentylsulfinyl group, a tert-pentylsulfinyl group, a neopentylsulfinyl group, a 2,3-dimethylpropylsulfinyl group, an 1-ethylpropylsulfinyl group, a 1-methylbutylsulfinyl group, a n-hexylsulfinyl group, an isohexylsulfinyl group, a 1,1,2-trimethylpropylsulfinyl group or the like. The "(C$_1$-C$_6$) alkylsulfonyl group" refers to a straight-chain or branched-chain alkylsulfonyl group of 1 to 6 carbon atoms, for example, a methylsulfonyl group, an ethylsulfonyl group, a n-propylsulfonyl group, an isopropylsulfonyl group, a n-butylsulfonyl group, a sec-butylsulfonyl group, a tert-butylsulfonyl group, a n-pentylsulfonyl group, an isopentylsulfonyl group, a tert-pentylsulfonyl group, a neopentylsulfonyl group, a 2,3-dimethylpropylsulfonyl group, an 1-ethylpropylsulfonyl group, a 1-methylbutylsulfonyl group, a n-hexylsulfonyl group, an isohexylsulfonyl group, a 1,1,2-trimethylpropylsulfonyl group or the like.

The "(C$_1$-C$_6$) alkylcarbonyl group" refers to a straight-chain or branched-chain alkylcarbonyl group of 1 to 6 carbon atoms, for example, a methylcarbonyl group, an ethylcarbonyl group, a n-propylcarbonyl group, an isopropylcarbonyl group, a n-butylcarbonyl group, a sec-butylcarbonyl group, a tert-butylcarbonyl group, a n-pentylcarbonyl group, an isopentylcarbonyl group, a tert-pentylcarbonyl group, a neopentylcarbonyl group, a 2,3-dimethylpropylcarbonyl group, an 1-ethylpropylcarbonyl group, a 1-methylbutylcarbonyl group, a n-hexylcarbonyl group, an isohexylcarbonyl group, a 1,1,2-trimethylpropylcarbonyl group or the like. The "(C$_1$-C$_6$) alkoxycarbonyl group" refers to a straight-chain or branched-chain alkoxycarbonyl group of 1 to 6 carbon atoms, for example, a methoxycarbonyl group, an ethoxycarbonyl group, a n-propoxycarbonyl group, an isopropoxycarbonyl group, a n-butoxycarbonyl group, a sec-butoxycarbonyl group, a tert-butoxycarbonyl group, a n-pentoxycarbonyl group, an isopentyloxycarbonyl group, a tert-pentyloxycarbonyl group, a neopentyloxycarbonyl group, a 2,3-dimethylpropyloxycarbonyl group, an 1-ethylpropyloxycarbonyl group, a 1-methylbutyloxycarbonyl group, a n-hexyloxycarbonyl group, an isohexyloxycarbonyl group, a 1,1,2-trimethylpropyloxycarbonyl group or the like.

The above-mentioned "(C$_1$-C$_6$) alkyl group", "(C$_2$-C$_6$) alkenyl group", "(C$_2$-C$_6$) alkynyl group", "(C$_3$-C$_6$) cycloalkyl group", "(C$_1$-C$_6$) alkoxy group", "(C$_2$-C$_6$) alkenyloxy group", "(C$_2$-C$_6$) alkynyloxy group", "(C$_3$-C$_6$) cycloalkyloxy group", "(C$_1$-C$_6$) alkylthio group", "(C$_1$-C$_6$) alkylsulfinyl group", "(C$_1$-C$_6$) alkylsulfonyl group", "(C$_2$-C$_6$) alkenylthio group", "(C$_2$-C$_6$) alkenylsulfinyl group", "(C$_2$-C$_6$) alkenylsulfonyl group", "(C$_2$-C$_6$) alkynylthio group", "(C$_2$-C$_6$) alkynylsulfinyl group", "(C$_2$-C$_6$) alkynylsulfonyl group", "(C$_3$-C$_6$) cycloalkylthio group", "(C$_3$-C$_6$) cycloalkylsulfinyl group" and "(C$_3$-C$_6$) cycloalkylsulfonyl group" may be substituted with one or more halogen atoms at a substitutable position(s) in place of a hydrogen atom(s), and in the case where any of the above-listed groups is substituted with two or more halogen atoms, the halogen atoms may be the same or different.

The above-mentioned "groups substituted with one or more halogen atoms" are expressed as a "halo (C$_1$-C$_6$) alkyl group", a "halo (C$_2$-C$_6$) alkenyl group", a "halo (C$_2$-C$_6$) alkynyl group", a "halo (C$_3$-C$_6$) cycloalkyl group", a "halo (C$_1$-C$_6$) alkoxy group", a "halo (C$_2$-C$_6$) alkenyloxy group", a "halo (C$_2$-C$_6$) alkynyloxy group", a "halo (C$_3$-C$_6$) cycloalkyloxy group", a "halo (C$_1$-C$_6$) alkylthio group", a "halo (C$_1$-C$_6$) alkylsulfinyl group", a "halo (C$_1$-C$_6$) alkylsulfonyl group", a "halo (C$_2$-C$_6$) alkenylthio group", a "halo (C$_2$-C$_6$) alkenylsulfinyl group", a "halo (C$_2$-C$_6$) alkenylsulfonyl group", a "halo (C$_2$-C$_6$) alkynylthio group", a "halo (C$_2$-C$_6$) alkynylsulfinyl group", a "halo (C$_2$-C$_6$) alkynylsulfonyl group", a "halo (C$_3$-C$_6$) cycloalkylthio group", a "halo (C$_3$-C$_6$) cycloalkylsulfinyl group" and a "halo (C$_3$-C$_6$) cycloalkylsulfonyl group".

The expressions "(C$_1$-C$_6$)", "(C$_2$-C$_6$)", "(C$_3$-C$_6$)", etc. each refer to the range of the number of carbon atoms in each group. The same definition holds true for groups in which two or more of the above-mentioned groups are coupled together, and for example, the "(C$_1$-C$_6$) alkoxy (C$_1$-C$_6$) alkyl group" means that a straight-chain or branched-chain alkoxy group of 1 to 6 carbon atoms is bound to a straight-chain or branched-chain alkyl group of 1 to 6 carbon atoms.

Examples of the salt of the oxime group-containing quinoline compound represented by the general formula (1) of the present invention or an N-oxide thereof include inorganic acid salts, such as hydrochlorides, sulfates, nitrates and phosphates; organic acid salts, such as acetates, fumarates, maleates, oxalates, methanesulfonates, benzenesulfonates and p-toluenesulfonates; and salts with an inorganic or organic base such as a sodium ion, a potassium ion, a calcium ion and a trimethylammonium ion.

The oxime group-containing quinoline compound represented by the general formula (1) of the present invention, an N-oxide thereof and a salt thereof can have one or more chiral centers in the structural formula, and can exist as two or more kinds of optical isomers or diastereomers. All the optical isomers and mixtures of the isomers at any ratio are also included in the present invention. Further, the oxime group-containing quinoline compound represented by the general formula (1) of the present invention and a salt thereof can exist as two kinds of geometric isomers due to a carbon-carbon double bond or a carbon-nitrogen double bond in the structural formula. All the geometric isomers and mixtures of the isomers at any ratio are also included in the present invention.

A preferable embodiment of the oxime group-containing quinoline compound represented by the general formula (1) of the present invention, an N-oxide thereof or a salt thereof is described as follows.

R$^1$ represents
(a1) a hydrogen atom;
(a2) a (C$_1$-C$_6$) alkyl group;
(a6) a (C$_3$-C$_6$) cycloalkyl (C$_1$-C$_6$) alkyl group;

(a7) a ($C_1$-$C_6$) alkoxy ($C_1$-$C_6$) alkyl group;
(a8) a halo ($C_1$-$C_6$) alkyl group;
(a11) a ($C_1$-$C_6$) alkylthio ($C_1$-$C_6$) alkyl group;
(a14) a ($C_1$-$C_6$) alkylsulfinyl ($C_1$-$C_6$) alkyl group;
(a15) a ($C_1$-$C_6$) alkylsulfonyl ($C_1$-$C_6$) alkyl group;
(a16) a ($C_1$-$C_6$) alkylcarbonyl group;
(a17) a ($C_1$-$C_6$) alkoxycarbonyl group;
(a18) a halo ($C_1$-$C_6$) alkylthio ($C_1$-$C_6$) alkyl group; or
(a19) a ($C_1$-$C_6$) alkyl (N≡CN═)S($C_1$-$C_6$) alkyl group,
$R^2$ represents
(b1) a hydrogen atom;
(b2) a ($C_1$-$C_6$) alkyl group; or
(b3) a cyano group,
$R^3$ represents
(c8) a halo ($C_1$-$C_6$) alkyl group;
(c15) a halo ($C_1$-$C_6$) alkylthio group; or
(c17) a halo ($C_1$-$C_6$) alkylsulfonyl group,
A represents an oxygen atom or N—$R^4$ (wherein $R^4$ represents a ($C_1$-$C_6$) alkyl group),
$A^1$ and $A^2$ each represent CH or a nitrogen atom,
m represents 2, and
n represents 1.

A more preferable embodiment of the oxime group-containing quinoline compound represented by the general formula (1) of the present invention, an N-oxide thereof or a salt thereof is described as follows.

$R^1$ represents
(a1) a hydrogen atom;
(a2) a ($C_1$-$C_6$) alkyl group;
(a6) a ($C_3$-$C_6$) cycloalkyl ($C_1$-$C_6$) alkyl group;
(a7) a ($C_1$-$C_6$) alkoxy ($C_1$-$C_6$) alkyl group;
(a8) a halo ($C_1$-$C_6$) alkyl group;
(a11) a ($C_1$-$C_6$) alkylthio ($C_1$-$C_6$) alkyl group;
(a14) a ($C_1$-$C_6$) alkylsulfinyl ($C_1$-$C_6$) alkyl group;
(a15) a ($C_1$-$C_6$) alkylsulfonyl ($C_1$-$C_6$) alkyl group;
(a16) a ($C_1$-$C_6$) alkylcarbonyl group;
(a17) a ($C_1$-$C_6$) alkoxycarbonyl group;
(a18) a halo ($C_1$-$C_6$) alkylthio ($C_1$-$C_6$) alkyl group; or
(a19) a ($C_1$-$C_6$) alkyl (N≡CN═)S($C_1$-$C_6$) alkyl group,
$R^2$ represents
(b1) a hydrogen atom; or
(b2) a ($C_1$-$C_6$) alkyl group,
$R^3$ represents
(c8) a halo ($C_1$-$C_6$) alkyl group;
(c15) a halo ($C_1$-$C_6$) alkylthio group; or
(c17) a halo ($C_1$-$C_6$) alkylsulfonyl group,
A represents an oxygen atom or N—$R^4$ (wherein $R^4$ represents a ($C_1$-$C_6$) alkyl group),
$A^1$ and $A^2$ may be the same or different, and each represent CH or a nitrogen atom,
m represents 2, and
n represents 1.

The oxime group-containing quinoline compound of the present invention or a salt thereof can be produced according to, for example, the production methods described below, which are non-limiting examples.

Production Method 1

[Chem. 2]

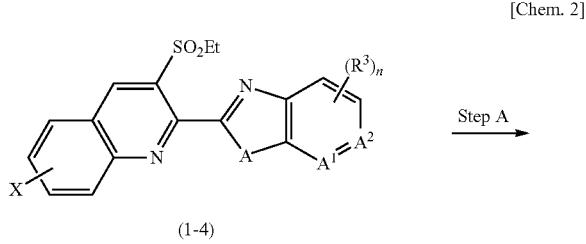

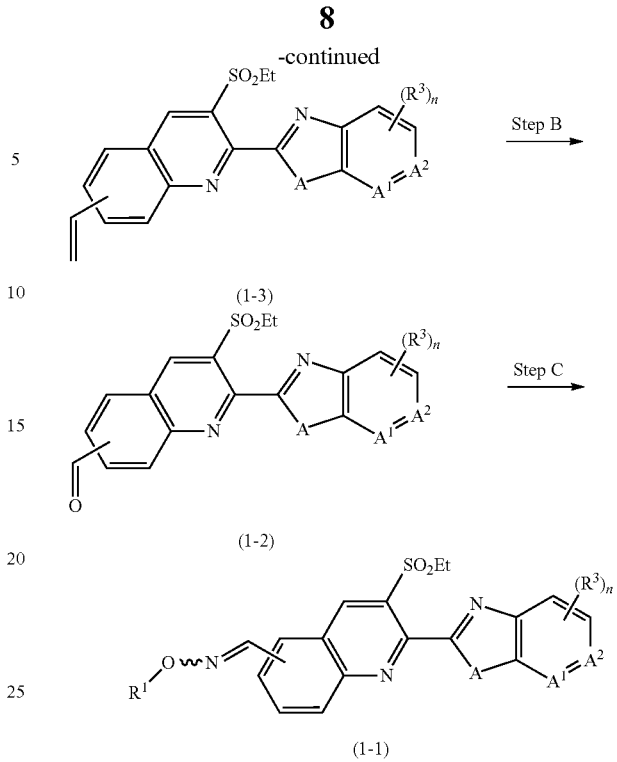

In the formula, $R^1$, $R^3$, A, $A^1$, $A^2$ and n are as defined above, and X represents a halogen atom.

Production Method at Step [A]

The quinoline compound represented by the general formula (1-3) can be produced by cross-coupling the haloquinoline compound represented by the general formula (1-4), which is produced by the method described in WO 2016/091731, with a vinylboronic acid compound in the presence of a metal catalyst and a base in an inert solvent.

Examples of the metal catalyst that can be used in this reaction include a palladium catalyst, a nickel catalyst, an iron catalyst, a ruthenium catalyst, a platinum catalyst, a rhodium catalyst and an iridium catalyst. Such a metal catalyst can be used in the form of "a metal", "a supported metal", "a metal salt such as a metal chloride, a metal bromide, a metal iodide, a metal nitrate, a metal sulfate, a metal carbonate, a metal oxalate, a metal acetate and a metal oxide", or "a complex compound such as an olefin complex, a phosphine complex, an amine complex, an ammine complex and an acetylacetonate complex". Preferred is a palladium catalyst.

Examples of the palladium catalyst include palladium metals such as palladium black and palladium sponge; and supported palladium metals such as palladium/alumina, palladium/carbon, palladium/silica and palladium/type Y zeolite. Also included are metal salts of palladium such as palladium chloride, palladium bromide, palladium iodide and palladium acetate. Other examples of the palladium catalyst include complex compounds of palladium such as t-allylpalladium chloride dimer, palladium acetylacetonate, dichlorobis(acetonitrile)palladium, dichlorobis(benzonitrile)palladium, bis(dibenzylideneacetone)palladium, tris(dibenzylideneacetone)dipalladium, tris(dibenzylideneacetone)dipalladium (chloroform adduct), dichlorodiammine palladium, dichlorobis(triphenylphosphine)palladium, dichlorobis(tricyclohexylphosphine)palladium, tetrakis(triphenylphosphine)palladium, dichloro[1,2-bis(diphenylphosphino)ethane]palladium, dichloro[1,3-bis(diphenylphosphino)propane]palladium, dichloro[1,4-bis(diphenylphosphino)butane]palladium, dichloro[1,1'-bis(diphenylphosphino)ferrocene]palladium and a [(diphenylphosphino)ferrocene]dichloropalladium-dichloromethane complex.

These palladium catalysts may be used alone or in combination with a tertiary phosphine. Examples of the tertiary phosphine that can be used in combination with the palladium catalyst include triphenylphosphine, trimethylphosphine, triethylphosphine, tributylphosphine, tri(tert-butyl) phosphine, tricyclohexylphosphine, tri-o-tolylphosphine, trioctylphosphine, 9,9-dimethyl-4,5-bis(diphenylphosphino) xanthene, 2-(di-tert-butylphosphino)biphenyl, 2-(dicyclohexylphosphino)biphenyl, 1,2-bis(diphenylphosphino)ethane, 1,3-bis(diphenylphosphino)propane, 1,4-bis(diphenylphosphino)butane, 1,1'-bis(diphenylphosphino) ferrocene, (R)-(+)-2,2'-bis(diphenylphosphino)-1,1'-binaphthyl, (S)-(−)-2,2'-bis(diphenylphosphino)-1,1'-binaphthyl and (±)-2,2'-bis(diphenylphosphino)-1,1'-binaphthyl.

Examples of the vinylboronic acid compound that can be used in this reaction include vinylmagnesium bromide, vinylmagnesium chloride, vinylzinc chloride, tributylvinyltin, potassium vinyltrifluoroborate, vinylboronic acid, vinylboronic anhydride, vinylboronic acid 2-methyl-2,4-pentanediol ester, vinylboronic acid pinacol ester and triethoxyvinylsilane.

Examples of the base that can be used in this reaction include inorganic bases such as sodium hydroxide, potassium hydroxide, sodium carbonate, potassium carbonate, cesium carbonate, sodium hydrogen carbonate and potassium hydrogen carbonate; alkali metal hydrides such as sodium hydride and potassium hydride; and alkoxides such as sodium methoxide, sodium ethoxide and potassium tert-butoxide. The amount of the base used is usually in the range of an about 1- to 5-fold molar amount relative to the condensed heterocyclic compound represented by the general formula (1-4).

The inert solvent used in this reaction may be any solvent that does not markedly inhibit the reaction, and examples include alcohols such as methanol, ethanol, propanol, butanol and 2-propanol; straight-chain or cyclic ethers such as diethyl ether, tetrahydrofuran, dioxane and dimethoxyethane (DME); aromatic hydrocarbons such as benzene, toluene and xylene; halogenated aliphatic hydrocarbons such as methylene chloride, chloroform and carbon tetrachloride; halogenated aromatic hydrocarbons such as chlorobenzene and dichlorobenzene; nitriles such as acetonitrile; esters such as ethyl acetate; polar solvents such as N,N-dimethylformamide, N,N-dimethylacetamide, dimethyl sulfoxide and 1,3-dimethyl-2-imidazolidinone; and water. One of these inert solvents may be used alone, and also two or more of them may be used as a mixture.

The reaction temperature in this reaction is usually in the range of about 0° C. to the boiling point of the solvent used. The reaction time varies with the reaction scale, the reaction temperature and the like, but is basically selected as appropriate from the range of a few minutes to 48 hours. This reaction may be conducted under the atmosphere of an inert gas such as nitrogen gas and argon gas. After the reaction is completed, the compound of interest is isolated from the post-reaction mixture by the usual method. As needed, recrystallization, column chromatography, etc. can be employed for the purification of the compound of interest.

Production Method at Step [B]

Firstly, the vinyl quinoline compound represented by the general formula (1-3) is reacted in the presence of osmium tetroxide and an oxidizing agent according to the method described in the Lecture of Experimental Chemistry (Jikken Kagaku Kouza), 4th edition, vol. 23, Organic Chemistry V, Oxidation Reaction (published by Maruzen Co., Ltd.) to yield a diol quinoline compound. The diol quinoline compound is then reacted in the presence of a periodic acid compound and an inert solvent according to the method described in the New Lecture of Experimental Chemistry (Shin Jikken Kagaku Kouza), vol. 15, Oxidation and Reduction I-1 (published by Maruzen Co., Ltd) to yield the formyl quinoline compound represented by the general formula (1-2). After the reaction is completed, the compound of interest is isolated from the post-reaction mixture by the usual method. As needed, recrystallization, column chromatography, etc. can be employed for the purification of the compound of interest.

Production Method at Step [C]

The oxime compound represented by the general formula (1-1) can be produced from the formyl quinoline compound represented by the general formula (1-2) according to the method described in ORGANIC FUNCTIONAL GROUP PREPARATIONS III, 2nd edition, ACADEMIC PRESS, INC. After the reaction is completed, the compound of interest is isolated from the post-reaction mixture by the usual method. As needed, recrystallization, column chromatography, etc. can be employed for the purification of the compound of interest.

Production Method 2

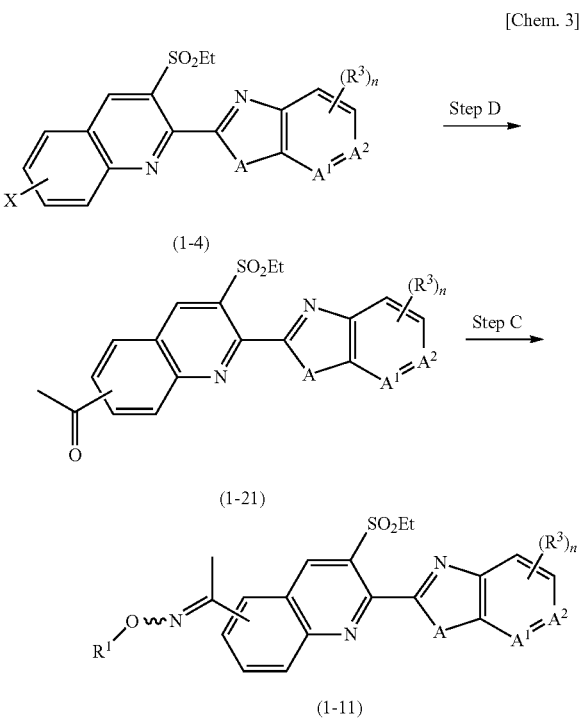

[Chem. 3]

In the formula, $R^1$, $R^3$, A, $A^1$, $A^2$ and n are as defined above, and X represents a halogen atom.

Production Method at Step [D]

The acetyl quinoline compound represented by the general formula (1-21) can be produced from the haloquinoline compound represented by the general formula (1-4) according to the method described in J. Org. Chem., 57, 1481 (1992) or WO 2010/089292. The acetyl quinoline compound is then reacted according to the production method at Step [C] to yield the oxime compound represented by the general formula (1-11).

Specific examples of the compound of the present invention are shown below. In the tables given below, Me stands for a methyl group, Et stands for an ethyl group, n-Pr stands for a n-propyl group, i-Pr stands for an isopropyl group, c-Pr stands for a cyclopropyl group, i-Bu stands for an isobutyl group, and t-Bu stands for a tert-butyl group. Shown in the column of "Physical property" is a melting point (° C.) or the presence of $^1$H-NMR data. $^1$H-NMR data are shown in Table 9.

[Chem. 4]

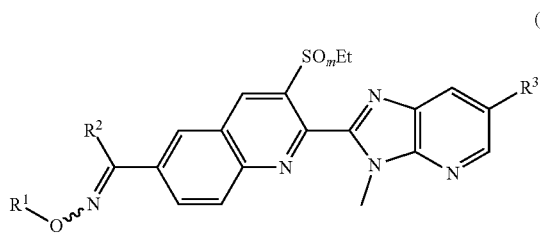

(1a)

TABLE 1

| Compound No. | $R^1$ | $R^2$ | $R^3$ | m | Physical property |
|---|---|---|---|---|---|
| 1-1 | H | H | $CF_3$ | 2 | 123-124 |
| 1-2 | H | Me | $CF_3$ | 2 | |
| 1-3 | Et | H | $CF_3$ | 2 | |
| 1-4 | Et | Me | $CF_3$ | 2 | |
| 1-5 | n-Pr | H | $CF_3$ | 2 | |
| 1-6 | n-Pr | Me | $CF_3$ | 2 | |
| 1-7 | $CH_2CF_3$ | H | $CF_3$ | 2 | 92-93 |
| 1-8 | $CH_2CF_3$ | Me | $CF_3$ | 2 | |
| 1-9 | $CH_2CF_3$ | Et | $CF_3$ | 2 | |
| 1-10 | $CH_2CF_3$ | CN | $CF_3$ | 2 | |
| 1-11 | $CH_2$-c-Pr | H | $CF_3$ | 2 | |
| 1-12 | $CH_2$-c-Pr | Me | $CF_3$ | 2 | |
| 1-13 | $CH_2CHF_2$ | H | $CF_3$ | 2 | |
| 1-14 | $CH_2CHF_2$ | Me | $CF_3$ | 2 | |
| 1-15 | $CH_2CF_2CHF_2$ | H | $CF_3$ | 2 | |
| 1-16 | $CH_2CF_2CHF_2$ | Me | $CF_3$ | 2 | |
| 1-17 | $CH_2CF_2CF_3$ | H | $CF_3$ | 2 | |
| 1-18 | $CH_2CF_2CF_3$ | Me | $CF_3$ | 2 | |
| 1-19 | $CH_2SMe$ | H | $CF_3$ | 2 | |
| 1-20 | $CH_2SMe$ | Me | $CF_3$ | 2 | |

TABLE 2

| Compound No. | $R^1$ | $R^2$ | $R^3$ | m | Physical property |
|---|---|---|---|---|---|
| 2-1 | H | H | $CF_3$ | 2 | 281-282 |
| 2-2 | H | Me | $CF_3$ | 2 | 170-171 |
| 2-3 | Et | H | $CF_3$ | 2 | 82-83 |
| 2-4 | Et | Me | $CF_3$ | 2 | |
| 2-5 | n-Pr | H | $CF_3$ | 2 | 80-81 |
| 2-6 | n-Pr | Me | $CF_3$ | 2 | |
| 2-7 | $CH_2CF_3$ | H | $CF_3$ | 2 | 164-165 |
| 2-8 | $CH_2CF_3$ | Me | $CF_3$ | 2 | 72-73 |
| 2-9 | $CH_2CF_3$ | Et | $CF_3$ | 2 | |
| 2-10 | $CH_2CF_3$ | CN | $CF_3$ | 2 | |
| 2-11 | $CH_2$-c-Pr | H | $CF_3$ | 2 | 72-73 |
| 2-12 | $CH_2$-c-Pr | Me | $CF_3$ | 2 | |
| 2-13 | $CH_2CHF_2$ | H | $CF_3$ | 2 | 87-88 |
| 2-14 | $CH_2CHF_2$ | Me | $CF_3$ | 2 | |
| 2-15 | $CH_2CF_2CHF_2$ | H | $CF_3$ | 2 | |
| 2-16 | $CH_2CF_2CHF_2$ | Me | $CF_3$ | 2 | |
| 2-17 | $CH_2CF_2CF_3$ | H | $CF_3$ | 2 | |
| 2-18 | $CH_2CF_2CF_3$ | Me | $CF_3$ | 2 | |
| 2-19 | $CH_2SMe$ | H | $CF_3$ | 2 | 70-71 |
| 2-20 | $CH_2SMe$ | Me | $CF_3$ | 2 | |

TABLE 3

| Compound No. | $R^1$ | $R^2$ | $R^3$ | m | Physical property |
|---|---|---|---|---|---|
| 2-21 | i-Pr | H | $CF_3$ | 2 | 86-87 |
| 2-22 | t-Bu | H | $CF_3$ | 2 | 110-111 |
| 2-23 | i-Bu | H | $CF_3$ | 2 | 83-84 |
| 2-24 | $CH_2SOMe$ | H | $CF_3$ | 2 | 163-164 |
| 2-25 | $CH_2SO_2Me$ | H | $CF_3$ | 2 | 74-75 |
| 2-26 | $CH_2CH_2SMe$ | H | $CF_3$ | 2 | 105-106 |
| 2-27 | $CH_2OMe$ | H | $CF_3$ | 2 | 259-260 |
| 2-28 | COMe | H | $CF_3$ | 2 | 175-176 |
| 2-29 | $CO_2Et$ | H | $CF_3$ | 2 | 122-123 |

TABLE 4

| Compound No. | $R^1$ | $R^2$ | $R^3$ | m | Physical property |
|---|---|---|---|---|---|
| 2-30 | $CH_2SEt$ | H | $CF_3$ | 2 | 63-64 |
| 2-31 | $CH_2SOEt$ | H | $CF_3$ | 2 | 94-95 |
| 2-32 | $CH_2SO_2Et$ | H | $CF_3$ | 2 | 85-86 |
| 2-33 | $CH_2Si$-Pr | H | $CF_3$ | 2 | 54-55 |
| 2-34 | $CH_2SOi$-Pr | H | $CF_3$ | 2 | 162-163 |
| 2-35 | $CH_2SO_2i$-Pr | H | $CF_3$ | 2 | 63-64 |
| 2-36 | $CH_2St$-Bu | H | $CF_3$ | 2 | 202-203 |
| 2-37 | $CH_2SOt$-Bu | H | $CF_3$ | 2 | 191-192 |
| 2-38 | $CH_2SO_2t$-Bu | H | $CF_3$ | 2 | 92-93 |
| 2-39 | $CH_2SCF_3$ | H | $CF_3$ | 2 | 99-100 |

[Chem. 5]

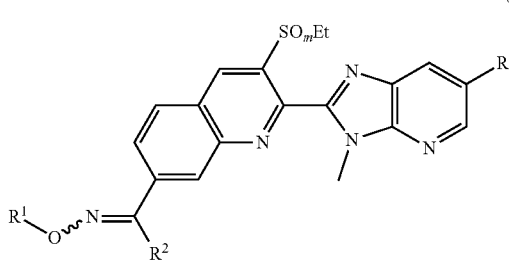

(1b)

[Chem. 6]

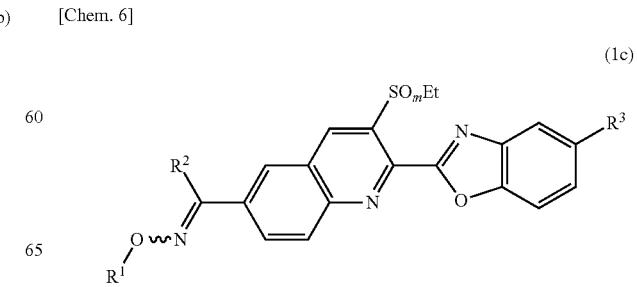

(1c)

TABLE 5

| Compound No. | R¹ | R² | R³ | m | Physical property |
|---|---|---|---|---|---|
| 3-1 | H | H | SCF$_3$ | 2 | 246-247 |
| 3-2 | H | Me | SCF$_3$ | 2 | NMR |
| 3-3 | Et | H | SCF$_3$ | 2 | |
| 3-4 | Et | Me | SCF$_3$ | 2 | |
| 3-5 | n-Pr | H | SCF$_3$ | 2 | |
| 3-6 | n-Pr | Me | SCF$_3$ | 2 | |
| 3-7 | CH$_2$CF$_3$ | H | SCF$_3$ | 2 | |
| 3-8 | CH$_2$CF$_3$ | Me | SCF$_3$ | 2 | 216-217 |
| 3-9 | CH$_2$CF$_3$ | Et | SCF$_3$ | 2 | |
| 3-10 | CH$_2$CF$_3$ | CN | SCF$_3$ | 2 | |
| 3-11 | CH$_2$-c-Pr | H | SCF$_3$ | 2 | |
| 3-12 | CH$_2$-c-Pr | Me | SCF$_3$ | 2 | |
| 3-13 | CH$_2$CHF$_2$ | H | SCF$_3$ | 2 | |
| 3-14 | CH$_2$CHF$_2$ | Me | SCF$_3$ | 2 | |
| 3-15 | CH$_2$CF$_2$CHF$_2$ | H | SCF$_3$ | 2 | |
| 3-16 | CH$_2$CF$_2$CHF$_2$ | Me | SCF$_3$ | 2 | |
| 3-17 | CH$_2$CF$_2$CF$_3$ | H | SCF$_3$ | 2 | |
| 3-18 | CH$_2$CF$_2$CF$_3$ | Me | SCF$_3$ | 2 | |
| 3-19 | CH$_2$SMe | H | SCF$_3$ | 2 | |
| 3-20 | CH$_2$SMe | Me | SO$_2$CF$_3$ | 2 | |

TABLE 6

| Compound No. | R¹ | R² | R³ | m | Physical property |
|---|---|---|---|---|---|
| 3-21 | H | H | SO$_2$CF$_3$ | 2 | 282-283 |
| 3-22 | H | Me | SO$_2$CF$_3$ | 2 | |
| 3-23 | Et | H | SO$_2$CF$_3$ | 2 | 237-238 |
| 3-24 | Et | Me | SO$_2$CF$_3$ | 2 | |
| 3-25 | n-Pr | H | SO$_2$CF$_3$ | 2 | |
| 3-26 | n-Pr | Me | SO$_2$CF$_3$ | 2 | |
| 3-27 | CH$_2$CF$_3$ | H | SO$_2$CF$_3$ | 2 | 254-255 |
| 3-28 | CH$_2$CF$_3$ | Me | SO$_2$CF$_3$ | 2 | |
| 3-29 | CH$_2$CF$_3$ | Et | SO$_2$CF$_3$ | 2 | |
| 3-30 | CH$_2$CF$_3$ | CN | SO$_2$CF$_3$ | 2 | |
| 3-31 | CH$_2$-c-Pr | H | SO$_2$CF$_3$ | 2 | |
| 3-32 | CH$_2$-c-Pr | Me | SO$_2$CF$_3$ | 2 | |
| 3-33 | CH$_2$CHF$_2$ | H | SO$_2$CF$_3$ | 2 | 242-243 |
| 3-34 | CH$_2$CHF$_2$ | Me | SO$_2$CF$_3$ | 2 | |
| 3-35 | CH$_2$CF$_2$CHF$_2$ | H | SO$_2$CF$_3$ | 2 | |
| 3-36 | CH$_2$CF$_2$CHF$_2$ | Me | SO$_2$CF$_3$ | 2 | |
| 3-37 | CH$_2$CF$_2$CF$_3$ | H | SO$_2$CF$_3$ | 2 | |
| 3-38 | CH$_2$CF$_2$CF$_3$ | Me | SO$_2$CF$_3$ | 2 | |
| 3-39 | CH$_2$SMe | H | SO$_2$CF$_3$ | 2 | |
| 3-40 | CH$_2$SMe | Me | SO$_2$CF$_3$ | 2 | |

[Chem. 7]

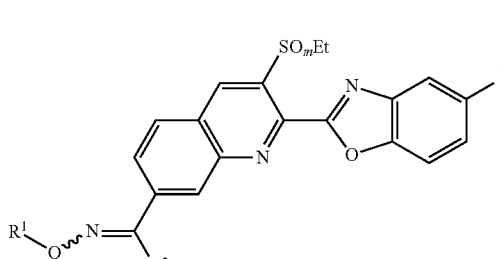

(1d)

TABLE 7

| Compound No. | R¹ | R² | R³ | m | Physical property |
|---|---|---|---|---|---|
| 4-1 | H | H | SCF$_3$ | 2 | |
| 4-2 | H | Me | SCF$_3$ | 2 | |
| 4-3 | Et | H | SCF$_3$ | 2 | |
| 4-4 | Et | Me | SCF$_3$ | 2 | |
| 4-5 | n-Pr | H | SCF$_3$ | 2 | |
| 4-6 | n-Pr | Me | SCF$_3$ | 2 | |
| 4-7 | CH$_2$CF$_3$ | H | SCF$_3$ | 2 | |
| 4-8 | CH$_2$CF$_3$ | Me | SCF$_3$ | 2 | |
| 4-9 | CH$_2$CF$_3$ | Et | SCF$_3$ | 2 | |
| 4-10 | CH$_2$CF$_3$ | CN | SCF$_3$ | 2 | |
| 4-11 | CH$_2$-c-Pr | H | SCF$_3$ | 2 | |
| 4-12 | CH$_2$-c-Pr | Me | SCF$_3$ | 2 | |
| 4-13 | CH$_2$CHF$_2$ | H | SCF$_3$ | 2 | |
| 4-14 | CH$_2$CHF$_2$ | Me | SCF$_3$ | 2 | |
| 4-15 | CH$_2$CF$_2$CHF$_2$ | H | SCF$_3$ | 2 | |
| 4-16 | CH$_2$CF$_2$CHF$_2$ | Me | SCF$_3$ | 2 | |
| 4-17 | CH$_2$CF$_2$CF$_3$ | H | SCF$_3$ | 2 | |
| 4-18 | CH$_2$CF$_2$CF$_3$ | Me | SCF$_3$ | 2 | |
| 4-19 | CH$_2$SMe | H | SCF$_3$ | 2 | |
| 4-20 | CH$_2$SMe | Me | SO$_2$CF$_3$ | 2 | |

TABLE 8

| Compound No. | R¹ | R² | R³ | m | Physical property |
|---|---|---|---|---|---|
| 4-21 | H | H | SO$_2$CF$_3$ | 2 | 269-270 |
| 4-22 | H | Me | SO$_2$CF$_3$ | 2 | |
| 4-23 | Et | H | SO$_2$CF$_3$ | 2 | |
| 4-24 | Et | Me | SO$_2$CF$_3$ | 2 | |
| 4-25 | n-Pr | H | SO$_2$CF$_3$ | 2 | 175-176 |
| 4-26 | n-Pr | Me | SO$_2$CF$_3$ | 2 | |
| 4-27 | CH$_2$CF$_3$ | H | SO$_2$CF$_3$ | 2 | 98-99 |
| 4-28 | CH$_2$CF$_3$ | Me | SO$_2$CF$_3$ | 2 | |
| 4-29 | CH$_2$CF$_3$ | Et | SO$_2$CF$_3$ | 2 | |
| 4-30 | CH$_2$CF$_3$ | CN | SO$_2$CF$_3$ | 2 | |
| 4-31 | CH$_2$-c-Pr | H | SO$_2$CF$_3$ | 2 | |
| 4-32 | CH$_2$-c-Pr | Me | SO$_2$CF$_3$ | 2 | |
| 4-33 | CH$_2$CHF$_2$ | H | SO$_2$CF$_3$ | 2 | |
| 4-34 | CH$_2$CHF$_2$ | Me | SO$_2$CF$_3$ | 2 | |
| 4-35 | CH$_2$CF$_2$CHF$_2$ | H | SO$_2$CF$_3$ | 2 | |
| 4-36 | CH$_2$CF$_2$CHF$_2$ | Me | SO$_2$CF$_3$ | 2 | |
| 4-37 | CH$_2$CF$_2$CF$_3$ | H | SO$_2$CF$_3$ | 2 | |
| 4-38 | CH$_2$CF$_2$CF$_3$ | Me | SO$_2$CF$_3$ | 2 | |
| 4-39 | CH$_2$SMe | H | SO$_2$CF$_3$ | 2 | 63-64 |
| 4-40 | CH$_2$SMe | Me | SO$_2$CF$_3$ | 2 | |
| 4-41 | i-Pr | H | SO$_2$CF$_3$ | 2 | 90-91 |

TABLE 9

| Compound No. | ¹H NMR Data |
|---|---|
| 3-2 | 9.14 (s, 1H), 8.45 (dd, 1H), 8.32 (d, 1H), 8.25 (d, 1H), 8.20 (s, 1H), 7.79 (d, 1H), 7.68 (d, 1H), 4.10 (q, 2H), 2.49 (s, 3H), 1.46 (t, 3H). |
| 5-1 | 9.03 (s, 1H), 8.24 (s, 2H), 8.17 (s, 1H), 8.03 (m, 2H), 7.69 (d, 1H), 7.53 (d, 1H), 3.84 (q, 2H), 3.83 (s, 3H), 1.39 (t, 3H). |

[Chem. 8]

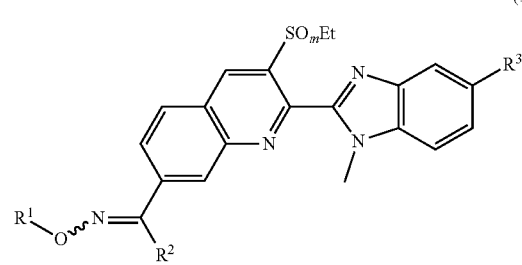

(1e)

TABLE 10

| Compound No. | R$^1$ | R$^2$ | R$^3$ | m | Physical property |
|---|---|---|---|---|---|
| 5-1 | H | H | SCF$_3$ | 2 | NMR |
| 5-2 | CH$_2$CHF$_2$ | H | SCF$_3$ | 2 | 65-66 |
| 5-3 | CH$_2$SMe | H | SCF$_3$ | 2 | 81-82 |
| 5-4 | H | H | SO$_2$CF$_3$ | 2 | 150-151 |
| 5-5 | CH$_2$CHF$_2$ | H | SO$_2$CF$_3$ | 2 | 97-98 |
| 5-6 | CH$_2$SMe | H | SO$_2$CF$_3$ | 2 | 100-101 |
| 5-7 | CH$_2$SOMe | H | SO$_2$CF$_3$ | 2 | 72-73 |
| 5-8 | CH$_2$SO$_2$Me | H | SO$_2$CF$_3$ | 2 | 94-95 |

[Chem. 9]

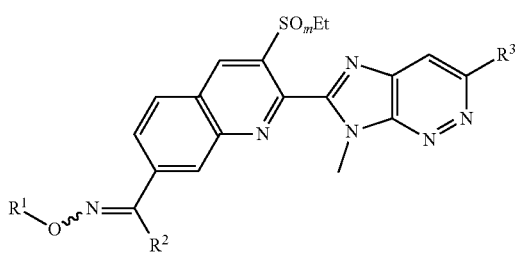

(1f)

TABLE 11

| Compound No. | R$^1$ | R$^2$ | R$^3$ | m | Physical property |
|---|---|---|---|---|---|
| 6-1 | H | H | C$_2$F$_5$ | 2 | 164-165 |
| 6-2 | i-Pr | H | C$_2$F$_5$ | 2 | 157-158 |
| 6-3 | CH$_2$SMe | H | C$_2$F$_5$ | 2 | 79-80 |
| 6-4 | CH$_2$SOMe | H | C$_2$F$_5$ | 2 | 109-110 |
| 6-5 | CH$_2$SO$_2$Me | H | C$_2$F$_5$ | 2 | 120-121 |
| 6-6 | H | H | CF$_3$ | 2 | 285-286 |
| 6-7 | CH$_2$CHF$_2$ | H | CF$_3$ | 2 | 105-106 |
| 6-8 | CH$_2$SMe | H | CF$_3$ | 2 | 86-87 |
| 6-9 | CH$_2$SOMe | H | CF$_3$ | 2 | 113-114 |
| 6-10 | CH$_2$SO$_2$Me | H | CF$_3$ | 2 | 110-111 |
| 6-11 | CH$_2$S(=NCN)Me | H | CF$_3$ | 2 | 63-64 |

The agricultural and horticultural insecticide comprising the oxime group-containing quinoline compound represented by the general formula (1) of the present invention or a salt thereof as an active ingredient is suitable for controlling a variety of pests which may damage paddy rice, fruit trees, vegetables, other crops and ornamental flowering plants. The target pests are, for example, agricultural and forest pests, horticultural pests, stored grain pests, sanitary pests, nematodes, etc.

Specific examples of the pests, nematodes, etc. include the following:

the species of the order Lepidoptera such as *Parasa consocia*, *Anomis mesogona*, *Papilio xuthus*, *Matsumuraeses azukivora*, *Ostrinia scapulalis*, *Spodoptera exempta*, *Hyphantria cunea*, *Ostrinia furnacalis*, *Pseudaletia separata*, *Tinea translucens*, *Bactra furfurana*, *Parnara guttata*, *Marasmia exigua*, *Parnara guttata*, *Sesamia inferens*, *Brachmia triannulella*, *Monema flavescens*, *Trichoplusia ni*, *Pleuroptya ruralis*, *Cystidia couaggaria*, *Lampides boeticus*, *Cephonodes hylas*, *Helicoverpa armigera*, *Phalerodonta manleyi*, *Eumeta japonica*, *Pieris brassicae*, *Malacosoma neustria testacea*, *Stathmopoda masinissa*, *Cuphodes diospyrosella*, *Archips xylosteanus*, *Agrotis segetum*, *Tetramoera schistaceana*, *Papilio machaon hippocrates*, *Endoclyta sinensis*, *Lyonetia prunifoliella*, *Phyllonorycter ringoneella*, *Cydia kurokoi*, *Eucoenogenes aestuosa*, *Lobesia botrana*, *Latoia sinica*, *Euzophera batangensis*, *Phalonidia mesotypa*, *Spilosoma imparilis*, *Glyphodes pyloalis*, *Olethreutes mori*, *Tineola bisselliella*, *Endoclyta excrescens*, *Nemapogon granellus*, *Synanthedon hector*, *Cydia pomonella*, *Plutella xylostella*, *Cnaphalocrocis medinalis*, *Sesamia calamistis*, *Scirpophaga incertulas*, *Pediasia teterrellus*, *Phthorimaea operculella*, *Stauropus fagi persimilis*, *Etiella zinckenella*, *Spodoptera exigua*, *Palpifer sexnotata*, *Spodoptera mauritia*, *Scirpophaga innotata*, *Xestia c-nigrum*, *Spodoptera depravata*, *Ephestia kuehniella*, *Angerona prunaria*, *Clostera anastomosis*, *Pseudoplusia includens*, *Matsumuraeses falcana*, *Helicoverpa assulta*, *Autographa nigrisigna*, *Agrotis ipsilon*, *Euproctis pseudoconspersa*, *Adoxophyes orana*, *Caloptilia theivora*, *Homona magnanima*, *Ephestia elutella*, *Eumeta minuscula*, *Clostera anachoreta*, *Heliothis maritima*, *Sparganothis pilleriana*, *Busseola fusca*, *Euproctis subflava*, *Biston robustum*, *Heliothis zea*, *Aedia leucomelas*, *Narosoideus flavidorsalis*, *Viminia rumicis*, *Bucculatrix pyrivorella*, *Grapholita molesta*, *Spulerina astaurota*, *Ectomyelois pyrivorella*, *Chilo suppressalis*, *Acrolepiopsis sapporensis*, *Plodia interpunctella*, *Hellula undalis*, *Sitotroga cerealella*, *Spodoptera litura*, a species of the family Tortricidae (*Eucosma aporema*), *Acleris comariana*, *Scopelodes contractus*, *Orgyia thyellina*, *Spodoptera frugiperda*, *Ostrinia zaguliaevi*, *Naranga aenescens*, *Andraca bipunctata*, *Paranthrene regalis*, *Acosmeryx castanea*, *Phyllocnistis toparcha*, *Endopiza viteana*, *Eupoecillia ambiguella*, *Anticarsia gemmatalis*, *Cnephasia cinereipalpana*, *Lymantria dispar*, *Dendrolimus spectabilis*, *Leguminivora glycinivorella*, *Maruca testulalis*, *Matsumuraeses phaseoli*, *Caloptilia soyella*, *Phyllocnistis citrella*, *Omiodes indicata*, *Archips fuscocupreanus*, *Acanthoplusia agnata*, *Bambalina* sp., *Carposina niponensis*, *Conogethes punctiferalis*, *Synanthedon* sp., *Lyonetia clerkella*, *Papilio helenus*, *Colias erate poliographus*, *Phalera flavescens*, the species of the family Pieridae such as *Pieris rapae crucivora* and *Pieris rapae*, *Euproctis similis*, *Acrolepiopsis suzukiella*, *Ostrinia nubilalis*, *Mamestra brassicae*, *Ascotis selenaria*, *Phtheochroides clandestina*, *Hoshinoa adumbratana*, *Odonestis pruni japonensis*, *Triaena intermedia*, *Adoxophyes orana fasciata*, *Grapholita inopinata*, *Spilonota ocellana*, *Spilonota lechriaspis*, *Illiberis pruni*, *Argyresthia conjugella*, *Caloptilia zachrysa*, *Archips brevipliccanus*, *Anomis flava*, *Pectinophora gossypiella*, *Notarcha derogata*, *Diaphania indica*, *Heliothis virescens* and *Earias cupreoviridis*;

the species of the order Hemiptera such as *Nezara antennata*, *Stenotus rubrovittatus*, *Graphosoma rubrolineatum*, *Trigonotylus coelestialium*, *Aeschynteles maculatus*, *Creontiades pallidifer*, *Dysdercus cingulatus*, *Chrysomphalus ficus*, *Aonidiella aurantii*, *Graptopsaltria nigrofuscata*, *Blissus leucopterus*, *Icerya purchasi*, *Piezodorus hybneri*, *Lagynotomus elongatus*, *Thaia subrufa*, *Scotinophara lurida*, *Sitobion ibarae*, *Stariodes iwasakii*, *Aspidiotus destructor*, *Taylorilygus pallidulus*, *Myzus mumecola*, *Pseudaulacaspis prunicola*, *Acyrthosiphon pisum*, *Anacanthocoris striicornis*, *Ectometopterus micantulus*, *Eysarcoris lewisi*, *Molipteryx fuliginosa*, *Cicadella viridis*, *Rhopalosophum rufiabdominalis*, *Saissetia oleae*, *Trialeurodes vaporariorum*, *Aguriahana quercus*, *Lygus* spp., *Euceraphis punctipennis*, *Andaspis kashicola*, *Coccus pseudomagnoliarum*, *Cavelerius saccharivorus*, *Galeatus spinifrons*, *Macrosiphoniella sanborni*, *Aonidiella citrina*, *Halyomorpha mista*, *Stephanitis fasciicarina*, *Trioza camphorae*, *Leptocorisa chinensis*, *Trioza quercicola*, *Uhlerites latius*, *Erythroneura comes*, *Paromius exiguus*, *Duplaspidiotus claviger*, *Nephotettix*

*nigropictus, Halticiellus insularis, Perkinsiella sacchari- cida, Psylla malivorella, Anomomeura mori, Pseudococcus longispinis, Pseudaulacaspis pentagona, Pulvinaria kuwa- cola, Apolygus lucorum, Togo hemipterus, Toxoptera auran- tii, Saccharicoccus sacchari, Geoica lucifuga, Numata muiri, Comstockaspis perniciosa, Unaspis citri, Aulacor- thum solani, Eysarcoris ventralis, Bemisia argentifolii, Cicadella spectra, Aspidiotus hederae, Liorhyssus hyalinus, Calophya nigridorsalis, Sogatella furcifera, Megoura cras- sicauda, Brevicoryne brassicae, Aphis glycines, Leptocorisa oratorius, Nephotettix virescens, Uroeucon formosanum, Cyrtopeltis tennuis, Bemisia tabaci, Lecanium persicae, Parlatoria theae, Pseudaonidia paeoniae, Empoasca onukii, Plautia stali, Dysaphis tulipae, Macrosiphum euphorbiae, Stephanitis pyrioides, Ceroplastes ceriferus, Parlatoria camelliae, Apolygus spinolai, Nephotettix cincticeps, Glau- cias subpunctatus, Orthotylus flavosparsus, Rhopalosiphum maidis, Peregrinus maidis, Eysarcoris parvus, Cimex lectu- larius, Psylla abieti, Nilaparvata lugens, Psylla tobirae, Eurydema rugosum, Schizaphis piricola, Psylla pyricola, Parlatoreopsis pyri, Stephanitis nashi, Dysmicoccus wis- tariae, Lepholeucaspis japonica, Sappaphis piri, Lipaphis erysimi, Neotoxoptera formosana, Rhopalosophum nympha- eae, Edwardsiana rosae, Pinnaspis aspidistrae, Psylla alni, Speusotettix subfusculus, Alnetoidia alneti, Sogatella pani- cicola, Adelphocoris lineolatus, Dysdercus poecilus, Parla- toria ziziphi, Uhlerites debile, Laodelphax striatellus, Eurydema pulchrum, Cletus trigonus, Clovia punctata, Empoasca* spp., *Coccus hesperidum, Pachybrachius luridus, Planococcus kraunhiae, Stenotus binotatus, Arboridia api- calis, Macrosteles fascifrons, Dolycoris baccarum, Adel- phocoris triannulatus, Viteus vitifolii, Acanthocoris sordi- dus, Leptocorisa acuta, Macropes obnubilus, Cletus punctiger, Riptortus clavatus, Paratrioza cockerelli, Aphro- phora costalis, Lygus disponsi, Lygus saundersi, Crisicoc- cus pini, Empoasca abietis, Crisicoccus matsumotoi, Aphis craccivora, Megacopta punctatissimum, Eysarcoris gutti- ger, Lepidosaphes beckii, Diaphorina citri, Toxoptera citri- cidus, Planococcus citri, Dialeurodes citri, Aleurocanthus spiniferus, Pseudococcus citriculus, Zyginella citri, Pulvi- naria citricola, Coccus discrepans, Pseudaonidia duplex, Pulvinaria aurantii, Lecanium corni, Nezara viridula, Stenodema calcaratum, Rhopalosiphum padi, Sitobion ake- biae, Schizaphis graminum, Sorhoanus tritici, Brachycau- dus helichrysi, Carpocoris purpureipennis, Myzus persicae, Hyalopterus pruni, Aphis farinose yanagicola, Metasalis populi, Unaspis yanonensis, Mesohomotoma camphorae, Aphis spiraecola, Aphis pomi, Lepidosaphes ulmi, Psylla mali, Heterocordylus flavipes, Myzus malisuctus, Aphidonu- guis mali, Orientus ishidai, Ovatus malicolens, Eriosoma lanigerum, Ceroplastes rubens* and *Aphis gossypii*;

the species of the order Coleoptera such as *Xystrocera globosa, Paederus fuscipes, Eucetonia roelofsi, Callosobru- chus chinensis, Cylas formicarius, Hypera postica, Echi- nocnemus squameus, Oulema oryzae, Donacia provosti, Lissorhoptrus oryzophilus, Colasposoma dauricum, Eus- cepes postfasciatus, Epilachna varivestis, Acanthoscelides obtectus, Diabrotica virgifera virgifera, Involvulus cupreus, Aulacophora femoralis, Bruchus pisorum, Epilachna vigin- tioctomaculata, Carpophilus dimidiatus, Cassida nebulosa, Luperomorpha tunebrosa, Phyllotreta striolata, Psacothea hilaris, Aeolesthes chrysothrix, Curculio sikkimensis, Car- pophilus hemipterus, Oxycetonia jucunda, Diabrotica* spp., *Mimela splendens, Sitophilus zeamais, Tribolium cas- taneum, Sitophilus oryzae, Palorus subdepressus, Melolon- tha japonica, Anoplophora malasiaca, Neatus picipes, Lep- tinotarsa decemlineata, Diabrotica undecimpunctata howardi, Sphenophorus venatus, Crioceris quatuordecim- punctata, Conotrachelus nenuphar, Ceuthorhynchidius albosuturalis, Phaedon brassicae, Lasioderma serricorne, Sitona japonicus, Adoretus tenuimaculatus, Tenebrio moli- tor, Basilepta balyi, Hypera nigrirostris, Chaetocnema con- cinna, Anomala cuprea, Heptophylla picea, Epilachna vigintioctopunctata, Diabrotica longicornis, Eucetonia pilif- era, Agriotes* spp., *Attagenus unicolor japonicus, Pagria signata, Anomala rufocuprea, Palorus ratzeburgii, Alphito- bius laevigatus, Anthrenus verbasci, Lyctus brunneus, Tri- bolium confusum, Medythia nigrobilineata, Xylotrechus pyr- rhoderus, Epitrix cucumeris, Tomicus piniperda, Monochamus alternatus, Popillia japonica, Epicauta gor- hami, Sitophilus zeamais, Rhynchites heros, Listroderes costirostris, Callosobruchus maculatus, Phyllobius arma- tus, Anthonomus pomorum, Linaeidea aenea* and *Anthono- mus grandis*;

the species of the order Diptera such as *Culex pipiens pallens, Pegomya hyoscyami, Liriomyza huidobrensis, Musca domestica, Chlorops oryzae, Hydrellia sasakii, Agro- myza oryzae, Hydrellia griseola, Hydrellia griseola, Oph- iomyia phaseoli, Dacus cucurbitae, Drosophila suzukii, Rhacochlaena japonica, Muscina stabulans*, the species of the family Phoridae such as *Megaselia spiracularis, Clog- mia albipunctata, Tipula aino, Phormia regina, Culex tri- taeniorhynchus, Anopheles sinensis, Hylemya brassicae, Asphondylia* sp., *Delia platura, Delia antiqua, Rhagoletis cerasi, Culex pipiens molestus Forskal, Ceratitis capitata, Bradysia agrestis, Pegomya cunicularia, Liriomyza sativae, Liriomyza bryoniae, Chromatomyia horticola, Liriomyza chinensis, Culex quinquefasciatus, Aedes aegypti, Aedes albopictus, Liriomyza trifolii, Liriomyza sativae, Dacus dor- salis, Dacus tsuneonis, Sitodiplosis mosellana, Meromuza nigriventris, Anastrepha ludens* and *Rhagoletis pomonella*;

the species of the order Hymenoptera such as *Pristomyrmex pungens*, the species of the family Bethylidae, *Monomorium pharaonis, Pheidole noda, Athalia rosae, Dryocosmus kuriphilus, Formica fusca japonica*, the species of the sub- family Vespinae, *Athalia infumata infumata, Arge pagana, Athalia japonica, Acromyrmex* spp., *Solenopsis* spp., *Arge mali* and *Ochetellus glaber*;

the species of the order Orthoptera such as *Homorocoryphus lineosus, Gryllotalpa* sp., *Oxya hyla intricata, Oxya yezoen- sis, Locusta migratoria, Oxya japonica, Homorocoryphus jezoensis* and *Teleogryllus emma*;

the species of the order Thysanoptera such as *Selenothrips rubrocinctus, Stenchaetothrips biformis, Haplothrips acu- leatus, Ponticulothrips diospyrosi, Thrips flavus, Anapho- thrips obscurus, Liothrips floridensis, Thrips simplex, Thrips nigropilosus, Heliothrips haemorrhoidalis, Pseudo- dendrothrips mori, Microcephalothrips abdominalis, Leeu- wenia pasanii, Litotetothrips pasaniae, Scirtothrips citri, Haplothrips chinensis, Mycterothrips glycines, Thrips seto- sus, Scirtothrips dorsalis, Dendrothrips minowai, Haplo- thrips niger, Thrips tabaci, Thrips alliorum, Thrips hawaiiensis, Haplothrips kurdjumovi, Chirothrips manica- tus, Frankliniella intonsa, Thrips coloratus, Franklinella occidentalis, Thrips palmi, Frankliniella lilivora* and *Lio- thrips vaneeckei*;

the species of the order Acari such as *Leptotrombidium akamushi, Tetranychus ludeni, Dermacentor variabilis, Tet- ranychus truncatus, Ornithonyssus bacoti, Demodex canis, Tetranychus viennensis, Tetranychus kanzawai*, the species of the family Ixodidae such as *Rhipicephalus sanguineus, Cheyletus malaccensis, Tyrophagus putrescentiae, Der- matophagoides farinae, Latrodectus hasseltii, Dermacentor taiwanicus, Acaphylla theavagrans, Polyphagotarsonemus*

*latus, Aculops lycopersici, Ornithonyssus sylvairum, Tetranychus urticae, Eriophyes chibaensis, Sarcoptes scabiei, Haemaphysalis longicornis, Ixodes scapularis, Tyrophagus similis, Cheyletus eruditus, Panonychus citri, Cheyletus moorei, Brevipalpus phoenicis, Octodectes cynotis, Dermatophagoides ptrenyssnus, Haemaphysalis flava, Ixodes ovatus, Phyllocoptruta citri, Aculus schlechtendali, Panonychus ulmi, Amblyomma americanum, Dermanyssus gallinae, Rhyzoglyphus robini* and *Sancassania* sp.;

the species of the order Isoptera such as *Reticulitermes miyatakei, Incisitermes minor, Coptotermes formosanus, Hodotermopsis japonica, Reticulitermes* sp., *Reticulitermes flaviceps amamianus, Glyptotermes kushimensis, Coptotermes guangzhoensis, Neotermes koshunensis, Glyptotermes kodamai, Glyptotermes satsumensis, Cryptotermes domesticus, Odontotermes formosanus, Glyptotermes nakajimai, Pericapritermes nitobei* and *Reticulitermes speratus;* the species of the order Blattodea such as *Periplaneta fuliginosa, Blattella germanica, Blatta orientalis, Periplaneta brunnea, Blattella lituricollis, Periplaneta japonica* and *Periplaneta americana;* the species of the order Siphonaptera such as *Pulex irritans, Ctenocephalides felis* and *Ceratophyllus gallinae;* the species of the phylum Nematoda such as *Nothotylenchus acris, Aphelenchoides besseyi, Pratylenchus penetrans, Meloidogyne hapla, Meloidogyne incognita, Globodera rostochiensis, Meloidogyne javanica, Heterodera glycines, Pratylenchus coffeae, Pratylenchus neglectus* and *Tylenchus semipenetrans;* and the species of the phylum Mollusca such as *Pomacea canaliculata, Achatina fulica, Meghimatium bilineatum, Lehmannina valentiana, Limax flavus* and *Acusta despecta sieboldiana.*

In addition, the agricultural and horticultural insecticide of the present invention has a strong insecticidal effect on *Tuta absoluta* as well.

Further, mites and ticks parasitic on animals are also included in the target pests, and the examples include the species of the family Ixodidae such as *Boophilus microplus, Rhipicephalus sanguineus, Haemaphysalis longicornis, Haemaphysalis flava, Haemaphysalis campanulata, Haemaphysalis concinna, Haemaphysalis japonica, Haemaphysalis kitaokai, Haemaphysalis ias, Ixodes ovatus, Ixodes nipponensis, Ixodes persulcatus, Amblyomma testudinarium, Haemaphysalis megaspinosa, Dermacentor reticulatus* and *Dermacentor taiwanesis; Dermanyssus gallinae;* the species of the genus *Ornithonyssus* such as *Ornithonyssus sylviarum* and *Ornithonyssus bursa;* the species of the family Trombiculidae such as *Eutrombicula wichmanni, Leptotrombidium akamushi, Leptotrombidium pallidum, Leptotrombidium fuji, Leptotrombidium tosa, Neotrombicula autumnalis, Eutrombicula alfreddugesi* and *Helenicula miyagawai;* the species of the family Cheyletidae such as *Cheyletiella yasguri, Cheyletiella parasitivorax* and *Cheyletiella blakei;* the species of the superfamily Sarcoptoidea such as *Psoroptes cuniculi, Chorioptes bovis, Otodectes cynotis, Sarcoptes scabiei* and *Notoedres cati;* and the species of the family Demodicidae such as *Demodex canis.*

Other target pests include fleas including ectoparasitic wingless insects belonging to the order Siphonaptera, more specifically, the species belonging to the families Pulicidae and Ceratophyllidae. Examples of the species belonging to the family Pulicidae include *Ctenocephalides canis, Ctenocephalides felis, Pulex irritans, Echidnophaga gallinacea, Xenopsylla cheopis, Leptopsylla segnis, Nosopsyllus fasciatus* and *Monopsyllus anisus.*

Other target pests include ectoparasites, for example, the species of the suborder Anoplura such as *Haematopinus eurysternus, Haematopinus asini, Dalmalinia ovis, Linognathus vituli, Haematopinus suis, Phthirus pubis* and *Pediculus capitis;* the species of the suborder Mallophaga such as *Trichodectes canis;* and hematophagous Dipteran insect pests such as *Tabanus trigonus, Culicoides schultzei* and *Simulium ornatum.* In addition, examples of endoparasites include nematodes such as lungworms, whipworms, nodular worms, endogastric parasitic worms, ascarides and filarial worms; cestodes such as *Spirometra erinacei, Diphyllobothrium latum, Dipylidium caninum, Multiceps multiceps, Echinococcus granulosus* and *Echinococcus multilocularis;* trematodes such as *Schistosoma japonicum* and *Fasciola hepatica;* and protozoa such as coccidia, Plasmodium, intestinal Sarcocystis, Toxoplasma and Cryptosporidium.

The agricultural and horticultural insecticide comprising the oxime group-containing quinoline compound represented by the general formula (1) of the present invention, an N-oxide thereof or a salt thereof as an active ingredient has a remarkable control effect on the above-described pests which damage lowland crops, field crops, fruit trees, vegetables, other crops, ornamental flowering plants, etc. The desired effect can be obtained when the agricultural and horticultural insecticide is applied to nursery facilities for seedlings, paddy fields, fields, fruit trees, vegetables, other crops, ornamental flowering plants, etc. and their seeds, paddy water, foliage, cultivation media such as soil, or the like around the expected time of pest infestation, i.e., before the infestation or upon the confirmation of the infestation. In particularly preferable embodiments, the application of the agricultural and horticultural insecticide utilizes so-called penetration and translocation. That is, nursery soil, soil in transplanting holes, plant foot, irrigation water, cultivation water in hydroponics, or the like is treated with the agricultural and horticultural insecticide to allow crops, ornamental flowering plants, etc. to absorb the compound of the present invention through the roots via soil or otherwise.

Examples of useful plants to which the agricultural and horticultural insecticide of the present invention can be applied include, but are not particularly limited to, cereals (e.g., rice, barley, wheat, rye, oats, corn, etc.), legumes (e.g., soybeans, azuki beans, broad beans, green peas, kidney beans, peanuts, etc.), fruit trees and fruits (e.g., apples, citrus fruits, pears, grapes, peaches, plums, cherries, walnuts, chestnuts, almonds, bananas, etc.), leaf and fruit vegetables (e.g., cabbages, tomatoes, spinach, broccoli, lettuce, onions, green onions (chives and Welsh onions), green peppers, eggplants, strawberries, pepper crops, okra, Chinese chives, etc.), root vegetables (e.g., carrots, potatoes, sweet potatoes, taros, Japanese radishes, turnips, lotus roots, burdock roots, garlic, Chinese scallions, etc.), crops for processing (e.g., cotton, hemp, beet, hops, sugarcane, sugar beet, olives, rubber, coffee, tobacco, tea, etc.), gourds (e.g., Japanese pumpkins, cucumbers, watermelons, oriental sweet melons, melons, etc.), pasture grass (e.g., orchardgrass, sorghum, timothy, clover, alfalfa, etc.), lawn grass (e.g., Korean lawn grass, bent grass, etc.), spice and aromatic crops and ornamental crops (e.g., lavender, rosemary, thyme, parsley, pepper, ginger, etc.), ornamental flowering plants (e.g., *chrysanthemum*, rose, carnation, orchid, tulip, lily, etc.), garden trees (e.g., ginkgo trees, cherry trees, Japanese *aucuba*, etc.) and forest trees (e.g., *Abies sachalinensis, Picea* jezoensis, pine, yellow cedar, Japanese cedar, hinoki cypress, *eucalyptus*, etc.).

The above-mentioned "plants" also include plants provided with herbicide tolerance by a classical breeding technique or a gene recombination technique. Examples of such herbicide tolerance include tolerance to HPPD inhibitors, such as isoxaflutole; ALS inhibitors, such as imazethapyr and thifensulfuron-methyl; EPSP synthase inhibitors, such as glyphosate; glutamine synthetase inhibitors, such as glufosinate; acetyl-CoA carboxylase inhibitors, such as sethoxydim; or other herbicides, such as bromoxynil, dicamba and 2,4-D.

Examples of the plants provided with herbicide tolerance by a classical breeding technique include varieties of rapeseed, wheat, sunflower and rice tolerant to the imidazolinone family of ALS-inhibiting herbicides such as imazethapyr, and such plants are sold under the trade name of Clearfield (registered trademark). Also included is a variety of soybean provided with tolerance to the sulfonyl urea family of ALS-inhibiting herbicides such as thifensulfuron-methyl by a classical breeding technique, and this is sold under the trade name of STS soybean. Also included are plants provided with tolerance to acetyl-CoA carboxylase inhibitors such as trione oxime herbicides and aryloxy phenoxy propionic acid herbicides by a classical breeding technique, for example, SR corn and the like.

Plants provided with tolerance to acetyl-CoA carboxylase inhibitors are described in Proc. Natl. Acad. Sci. USA, 87, 7175-7179 (1990), and the like. Further, acetyl-CoA carboxylase mutants resistant to acetyl-CoA carboxylase inhibitors are reported in Weed Science, 53, 728-746 (2005), and the like, and by introducing the gene of such an acetyl-CoA carboxylase mutant into plants by a gene recombination technique, or introducing a resistance-conferring mutation into acetyl-CoA carboxylase of plants, plants tolerant to acetyl-CoA carboxylase inhibitors can be engineered. Alternatively, by introducing a nucleic acid causing base substitution mutation into plant cells (a typical example of this technique is chimeraplasty technique (Gura T. 1999. Repairing the Genome's Spelling Mistakes. Science 285: 316-318.)) to allow site-specific substitution mutation in the amino acids encoded by an acetyl-CoA carboxylase gene, an ALS gene or the like of plants, plants tolerant to acetyl-CoA carboxylase inhibitors, ALS inhibitors or the like can be engineered. The agricultural and horticultural insecticide of the present invention can be applied to these plants as well.

Further, exemplary toxins expressed in genetically modified plants include insecticidal proteins of *Bacillus cereus* or *Bacillus popilliae*; *Bacillus thuringiensis* δ-endotoxins, such as Cry1Ab, Cry1Ac, Cry1F, Cry1Fa2, Cry2Ab, Cry3A, Cry3Bb1 and Cry9C, and other insecticidal proteins, such as VIP1, VIP2, VIP3 and VIP3A; nematode insecticidal proteins; toxins produced by animals, such as scorpion toxins, spider toxins, bee toxins and insect-specific neurotoxins; toxins of filamentous fungi; plant lectins; agglutinin; protease inhibitors, such as trypsin inhibitors, serine protease inhibitors, patatin, cystatin and papain inhibitors; ribosome inactivating proteins (RIP), such as ricin, maize RIP, abrin, luffin, saporin and bryodin; steroid metabolizing enzymes, such as 3-hydroxy steroid oxidase, ecdysteroid-UDP-glucosyltransferase and cholesterol oxidase; ecdysone inhibitors; HMG-CoA reductase; ion channel inhibitors, such as sodium channel inhibitors and calcium channel inhibitors; juvenile hormone esterase; diuretic hormone receptors; stilbene synthase; bibenzyl synthase; chitinase; and glucanase.

Also included are hybrid toxins, partially deficient toxins and modified toxins derived from the following: δ-endotoxin proteins such as Cry1Ab, Cry1Ac, Cry1F, Cry1Fa2, Cry2Ab, Cry3A, Cry3Bb1, Cry9C, Cry34Ab and Cry35Ab, and other insecticidal proteins such as VIP1, VIP2, VIP3 and VIP3A. The hybrid toxin can be produced by combining some domains of these proteins differently from the original combination in nature with the use of a recombination technique. As the partially deficient toxin, a Cry1Ab toxin in which a part of the amino acid sequence is deleted is known. In the modified toxin, one or more amino acids of a naturally occurring toxin are substituted.

Examples of the foregoing toxins and genetically modified plants capable of synthesizing these toxins are described in EP-A-0 374 753, WO 93/07278, WO 95/34656, EP-A-0 427 529, EP-A-451 878, WO 03/052073, etc.

Due to the toxins contained in such genetically modified plants, the plants exhibit resistance to pests, in particular, Coleopteran insect pests, Hemipteran insect pests, Dipteran insect pests, Lepidopteran insect pests and nematodes. The above-described technologies and the agricultural and horticultural insecticide of the present invention can be used in combination or used systematically.

In order to control target pests, the agricultural and horticultural insecticide of the present invention, with or without appropriate dilution or suspension in water etc., is applied to plants potentially infested with the target insect pests or nematodes in an amount effective for the control of the insect pests or nematodes. For example, in order to control insect pests and nematodes that may damage crop plants such as fruit trees, cereals and vegetables, foliar application and seed treatment such as dipping, dust coating and calcium peroxide coating can be performed. Further, treatment of soil or the like may also be performed to allow plants to absorb agrochemicals through their roots. Examples of such treatment include whole soil incorporation, planting row treatment, bed soil incorporation, plug seedling treatment, planting hole treatment, plant foot treatment, top-dressing, treatment of nursery boxes for paddy rice, and submerged application. In addition, application to culture media in hydroponics, smoking treatment, trunk injection and the like can also be performed.

Further, the agricultural and horticultural insecticide of the present invention, with or without appropriate dilution or suspension in water etc., can be applied to sites potentially infested with pests in an amount effective for the control of the pests. For example, it can be directly applied to stored grain pests, house pests, sanitary pests, forest pests, etc., and also be used for coating of residential building materials, for smoking treatment, or as a bait formulation.

Exemplary methods of seed treatment include dipping of seeds in a diluted or undiluted fluid of a liquid or solid formulation for the permeation of agrochemicals into the seeds; mixing or dust coating of seeds with a solid or liquid formulation for the adherence of the formulation onto the surfaces of the seeds; coating of seeds with a mixture of a solid or liquid formulation and an adhesive carrier such as resins and polymers; and application of a solid or liquid formulation to the vicinity of seeds at the same time as seeding.

The term "seed" in the above-mentioned seed treatment refers to a plant body which is in the early stages of cultivation and used for plant propagation. The examples include, in addition to a so-called seed, a plant body for vegetative propagation, such as a bulb, a tuber, a seed potato, a bulbil, a propagule, a discoid stem and a stem used for cuttage.

The term "soil" or "cultivation medium" in the method of the present invention for using an agricultural and horticultural insecticide refers to a support medium for crop cultivation, in particular a support medium which allows crop plants to spread their roots therein, and the materials are not particularly limited as long as they allow plants to grow. Examples of the support medium include what is called soils, seedling mats and water, and specific examples of the materials include sand, pumice, vermiculite, diatomite, agar, gelatinous substances, high-molecular-weight substances, rock wool, glass wool, wood chip and bark.

Exemplary methods of the application to crop foliage or to stored grain pests, house pests, sanitary pests, forest pests, etc. include application of a liquid formulation, such as an emulsifiable concentrate and a flowable, or a solid formulation, such as a wettable powder and a water-dispersible granule, after appropriate dilution in water; dust application; and smoking.

Exemplary methods of soil application include application of a water-diluted or undiluted liquid formulation to the foot of plants, nursery beds for seedlings, or the like; application of a granule to the foot of plants, nursery beds for seedlings, or the like; application of a dust, a wettable powder, a water-dispersible granule, a granule or the like onto soil and subsequent incorporation of the formulation into the whole soil before seeding or transplanting; and application of a dust, a wettable powder, a water-dispersible granule, a granule or the like to planting holes, planting rows or the like before seeding or planting.

To nursery boxes for paddy rice, for example, a dust, a water-dispersible granule, a granule or the like can be applied, although the suitable formulation may vary depending on the application timing, in other words, depending on the cultivation stage such as seeding time, greening period and planting time. A formulation such as a dust, a water-dispersible granule and a granule may be mixed with nursery soil. For example, such a formulation is incorporated into bed soil, covering soil or the whole soil. Simply, nursery soil and such a formulation may be alternately layered.

In the application to paddy fields, a solid formulation, such as a jumbo, a pack, a granule and a water-dispersible granule, or a liquid formulation, such as a flowable and an emulsifiable concentrate, is applied usually to flooded paddy fields. In a rice planting period, a suitable formulation, as it is or after mixed with a fertilizer, may be applied onto soil or injected into soil. In addition, an emulsifiable concentrate, a flowable or the like may be applied to the source of water supply for paddy fields, such as a water inlet and an irrigation device. In this case, treatment can be accomplished with the supply of water and thus achieved in a labor-saving manner.

In the case of field crops, their seeds, cultivation media in the vicinity of their plants, or the like may be treated in the period of seeding to seedling culture. In the case of plants of which the seeds are directly sown in the field, in addition to direct seed treatment, plant foot treatment during cultivation is preferable. Specifically, the treatment can be performed by, for example, applying a granule onto soil, or drenching soil with a formulation in a water-diluted or undiluted liquid form. Another preferable treatment is incorporation of a granule into cultivation media before seeding.

In the case of culture plants to be transplanted, preferable examples of the treatment in the period of seeding to seedling culture include, in addition to direct seed treatment, drench treatment of nursery beds for seedlings with a formulation in a liquid form; and granule application to nursery beds for seedlings. Also included are treatment of planting holes with a granule; and incorporation of a granule into cultivation media in the vicinity of planting points at the time of fix planting.

The agricultural and horticultural insecticide of the present invention is commonly used as a formulation convenient for application, which is prepared by the usual method for preparing agrochemical formulations.

That is, the oxime group-containing quinoline compound represented by the general formula (1) of the present invention or a salt thereof and an appropriate inactive carrier, and if needed an adjuvant, are blended in an appropriate ratio, and through the step of dissolution, separation, suspension, mixing, impregnation, adsorption and/or adhesion, are formulated into an appropriate form for application, such as a suspension concentrate, an emulsifiable concentrate, a soluble concentrate, a wettable powder, a water-dispersible granule, a granule, a dust, a tablet and a pack.

The composition (agricultural and horticultural insecticide or animal parasite control agent) of the present invention can optionally contain an additive usually used for agrochemical formulations or animal parasite control agents in addition to the active ingredient. Examples of the additive include carriers such as solid or liquid carriers, surfactants, dispersants, wetting agents, binders, tackifiers, thickeners, colorants, spreaders, sticking/spreading agents, antifreezing agents, anti-caking agents, disintegrants and stabilizing agents. If needed, preservatives, plant fragments, etc. may also be used as the additive. One of these additives may be used alone, and also two or more of them may be used in combination.

Examples of the solid carriers include natural minerals, such as quartz, clay, kaolinite, pyrophyllite, sericite, talc, bentonite, acid clay, attapulgite, zeolite and diatomite; inorganic salts, such as calcium carbonate, ammonium sulfate, sodium sulfate and potassium chloride; organic solid carriers, such as synthetic silicic acid, synthetic silicates, starch, cellulose and plant powders (for example, sawdust, coconut shell, corn cob, tobacco stalk, etc.); plastics carriers, such as polyethylene, polypropylene and polyvinylidene chloride; urea; hollow inorganic materials; hollow plastic materials; and fumed silica (white carbon). One of these solid carriers may be used alone, and also two or more of them may be used in combination.

Examples of the liquid carriers include alcohols including monohydric alcohols, such as methanol, ethanol, propanol, isopropanol and butanol, and polyhydric alcohols, such as ethylene glycol, diethylene glycol, propylene glycol, hexylene glycol, polyethylene glycol, polypropylene glycol and glycerin; polyol compounds, such as propylene glycol ether; ketones, such as acetone, methyl ethyl ketone, methyl isobutyl ketone, diisobutyl ketone and cyclohexanone; ethers, such as ethyl ether, dioxane, ethylene glycol monoethyl ether, dipropyl ether and tetrahydrofuran; aliphatic hydrocarbons, such as normal paraffin, naphthene, isoparaffin, kerosene and mineral oil; aromatic hydrocarbons, such as benzene, toluene, xylene, solvent naphtha and alkyl naphthalene; halogenated hydrocarbons, such as dichloromethane, chloroform and carbon tetrachloride; esters, such as ethyl acetate, diisopropyl phthalate, dibutyl phthalate, dioctyl phthalate and dimethyl adipate; lactones, such as γ-butyrolactone; amides, such as dimethylformamide, diethylformamide, dimethylacetamide and N-alkyl pyrrolidinone; nitriles, such as acetonitrile; sulfur compounds, such as dimethyl sulfoxide; vegetable oils, such as soybean oil, rapeseed oil, cotton seed oil and castor oil; and water. One of these liquid carriers may be used alone, and also two or more of them may be used in combination.

Exemplary surfactants used as the dispersant or the wetting/spreading agent include nonionic surfactants, such as sorbitan fatty acid ester, polyoxyethylene sorbitan fatty acid ester, sucrose fatty acid ester, polyoxyethylene fatty acid ester, polyoxyethylene resin acid ester, polyoxyethylene fatty acid diester, polyoxyethylene alkyl ether, polyoxyethylene alkyl aryl ether, polyoxyethylene alkyl phenyl ether, polyoxyethylene dialkyl phenyl ether, polyoxyethylene alkyl phenyl ether-formaldehyde condensates, polyoxyethylene-polyoxypropylene block copolymers, polystyrene-polyoxyethylene block polymers, alkyl polyoxyethylene-polypropylene block copolymer ether, polyoxyethylene alkylamine, polyoxyethylene fatty acid amide, polyoxyethylene fatty acid bis(phenyl ether), polyalkylene benzyl phenyl ether, polyoxyalkylene styryl phenyl ether, acetylene diol, polyoxyalkylene-added acetylene diol, polyoxyethylene ether-type silicone, ester-type silicone, fluorosurfactants, polyoxyethylene castor oil and polyoxyethylene hydrogenated castor oil; anionic surfactants, such as alkyl sulfates, polyoxyethylene alkyl ether sulfates, polyoxyethylene alkyl phenyl ether sulfates, polyoxyethylene styryl phenyl ether sulfates, alkylbenzene sulfonates, alkylaryl sulfonates, lignosulfonates, alkyl sulfosuccinates, naphthalene sulfonates, alkylnaphthalene sulfonates, salts of naphthalenesulfonic acid-formaldehyde condensates, salts of alkylnaphthalenesulfonic acid-formaldehyde condensates, fatty acid salts, polycarboxylic acid salts, polyacrylates, N-methyl-fatty acid sarcosinates, resinates, polyoxyethylene alkyl ether phosphates and polyoxyethylene alkyl phenyl ether phosphates; cationic surfactants including alkyl amine salts, such as lauryl amine hydrochloride, stearyl amine hydrochloride, oleyl amine hydrochloride, stearyl amine acetate, stearyl aminopropyl amine acetate, alkyl trimethyl ammonium chloride and alkyl dimethyl benzalkonium chloride; and amphoteric surfactants, such as amino acid-type or betaine-type amphoteric surfactants. One of these surfactants may be used alone, and also two or more of them may be used in combination.

Examples of the binders or the tackifiers include carboxymethyl cellulose or salts thereof, dextrin, soluble starch, xanthan gum, guar gum, sucrose, polyvinyl pyrrolidone, gum arabic, polyvinyl alcohol, polyvinyl acetate, sodium polyacrylate, polyethylene glycols with an average molecular weight of 6,000 to 20,000, polyethylene oxides with an average molecular weight of 100,000 to 5,000,000, phospholipids (for example, cephalin, lecithin, etc.), cellulose powder, dextrin, modified starch, polyaminocarboxylic acid chelating compounds, cross-linked polyvinyl pyrrolidone, maleic acid-styrene copolymers, (meth)acrylic acid copolymers, half esters of polyhydric alcohol polymer and dicarboxylic anhydride, water soluble polystyrene sulfonates, paraffin, terpene, polyamide resins, polyacrylates, polyoxyethylene, waxes, polyvinyl alkyl ether, alkylphenol-formaldehyde condensates and synthetic resin emulsions.

Examples of the thickeners include water soluble polymers, such as xanthan gum, guar gum, diutan gum, carboxymethyl cellulose, polyvinyl pyrrolidone, carboxyvinyl polymers, acrylic polymers, starch compounds and polysaccharides; and inorganic fine powders, such as high grade bentonite and fumed silica (white carbon).

Examples of the colorants include inorganic pigments, such as iron oxide, titanium oxide and Prussian blue; and organic dyes, such as alizarin dyes, azo dyes and metal phthalocyanine dyes.

Examples of the antifreezing agents include polyhydric alcohols, such as ethylene glycol, diethylene glycol, propylene glycol and glycerin.

Examples of the adjuvants serving to prevent caking or facilitate disintegration include polysaccharides (starch, alginic acid, mannose, galactose, etc.), polyvinyl pyrrolidone, fumed silica (white carbon), ester gum, petroleum resin, sodium tripolyphosphate, sodium hexametaphosphate, metal stearates, cellulose powder, dextrin, methacrylate copolymers, polyvinyl pyrrolidone, polyaminocarboxylic acid chelating compounds, sulfonated styrene-isobutylene-maleic anhydride copolymers and starch-polyacrylonitrile graft copolymers.

Examples of the stabilizing agents include desiccants, such as zeolite, quicklime and magnesium oxide; antioxidants, such as phenolic compounds, amine compounds, sulfur compounds and phosphoric acid compounds; and ultraviolet absorbers, such as salicylic acid compounds and benzophenone compounds.

Examples of the preservatives include potassium sorbate and 1,2-benzothiazolin-3-one.

Further, other adjuvants including functional spreading agents, activity enhancers such as metabolic inhibitors (piperonyl butoxide etc.), antifreezing agents (propylene glycol etc.), antioxidants (BHT etc.) and ultraviolet absorbers can also be used if needed.

The amount of the active ingredient compound in the agricultural and horticultural insecticide of the present invention can be adjusted as needed, and basically, the amount of the active ingredient compound is appropriately selected from the range of 0.01 to 90 parts by weight in 100 parts by weight of the agricultural and horticultural insecticide. For example, in the case where the agricultural and horticultural insecticide is a dust, a granule, an emulsifiable concentrate or a wettable powder, it is suitable that the amount of the active ingredient compound is 0.01 to 50 parts by weight (0.01 to 50% by weight relative to the total weight of the agricultural and horticultural insecticide).

The application rate of the agricultural and horticultural insecticide of the present invention may vary with various factors, for example, the purpose, the target pest, the growing conditions of crops, the tendency of pest infestation, the weather, the environmental conditions, the dosage form, the application method, the application site, the application timing, etc., but basically, the application rate of the active ingredient compound is appropriately selected from the range of 0.001 g to 10 kg, and preferably 0.01 g to 1 kg per 10 ares depending on the purpose.

Furthermore, for the expansion of the range of target pests and the appropriate time for pest control, or for dose reduction, the agricultural and horticultural insecticide of the present invention can be used after mixed with other agricultural and horticultural insecticides, acaricides, nematicides, microbicides, biopesticides and/or the like. Further, the agricultural and horticultural insecticide can be used after mixed with herbicides, plant growth regulators, fertilizers and/or the like depending on the situation.

Examples of such additional agricultural and horticultural insecticides, acaricides and nematicides used for the above-mentioned purposes include 3,5-xylyl methylcarbamate (XMC), crystalline protein toxins produced by *Bacillus thuringiensis* such as *Bacillus thuringiensis aizawai, Bacillus thuringiensis israelensis, Bacillus thuringiensis japonensis, Bacillus thuringiensis kurstaki* and *Bacillus thuringiensis tenebrionis*, BPMC, Bt toxin-derived insecticidal compounds, CPCBS (chlorfenson), DCIP (dichlorodiisopropyl ether), D-D (1,3-dichloropropene), DDT, NAC, O-4-dimethylsulfamoylphenyl O,O-diethyl phosphorothioate (DSP), O-ethyl O-4-nitrophenyl phenylphosphonothioate (EPN), tripropylisocyanurate (TPIC), acrinathrin, azadirachtin, azinphos-methyl, acequinocyl, acetamiprid, acetoprole, acephate, abamectin, avermectin-B, amidoflumet, amitraz, alanycarb, aldicarb, aldoxycarb, aldrin, alphaendosulfan, alpha-cypermethrin, albendazole, allethrin, isazofos, isamidofos, isoamidofos isoxathion, isofenphos, isoprocarb (MIPC), ivermectin, imicyafos, imidacloprid, imiprothrin, indoxacarb, esfenvalerate, ethiofencarb, ethion, ethiprole, etoxazole, ethofenprox, ethoprophos, etrimfos, emamectin, emamectin-benzoate, endosulfan, empenthrin, oxamyl, oxydemeton-methyl, oxydeprofos (ESP), oxibendazole, oxfendazole, potassium oleate, sodium oleate, cadusafos, cartap, carbaryl, carbosulfan, carbofuran, gamma-cyhalothrin, xylylcarb, quinalphos, kinoprene, chinomethionat, cloethocarb, clothianidin, clofentezine, chromafenozide, chlorantraniliprole, chlorethoxyfos, chlordimeform, chlordane, chlorpyrifos, chlorpyrifos-methyl, chlorphenapyr, chlorfenson, chlorfenvinphos, chlorfluazuron, chlorbenzilate, chlorobenzoate, kelthane (dicofol), salithion, cyanophos (CYAP), diafenthiuron, diamidafos, cyantraniliprole, theta-cypermethrin, dienochlor, cyenopyrafen, dioxabenzofos, diofenolan, sigma-cypermethrin, dichlofenthion (ECP), cycloprothrin, dichlorvos (DDVP), disulfoton, dinotefuran, cyhalothrin, cyphenothrin, cyfluthrin, diflubenzuron, cyflumetofen, diflovidazin, cyhexatin, cypermethrin, dimethylvinphos, dimethoate, dimeflufthrin, silafluofen, cyromazine, spinetoram, spinosad, spirodiclofen, spirotetramat, spiromesifen, sulfluramid, sulprofos, sulfoxaflor, zeta-cypermethrin, diazinon, tau-fluvalinate, dazomet, thiacloprid, thiamethoxam, thiodicarb, thiocyclam, thiosultap, thiosultap-sodium, thionazin, thiometon, deet, dieldrin, tetrachlorvinphos, tetradifon, tetramethylfluthrin, tetramethrin, tebupirimfos, tebufenozide, tebufenpyrad, tefluthrin, teflubenzuron, demeton-S-methyl, temephos, deltamethrin, terbufos, tralopyril, tralomethrin, transfluthrin, triazamate, triazuron, trichlamide, trichlorphon (DEP), triflumuron, tolfenpyrad, naled (BRP), nithiazine, nitenpyram, novaluron, noviflumuron, hydroprene, vaniliprole, vamidothion, parathion, parathion-methyl, halfenprox, halofenozide, bistrifluron, bisultap, hydramethylnon, hydroxy propyl starch, binapacryl, bifenazate, bifenthrin, pymetrozine, pyraclofos, pyrafluprole, pyridafenthion, pyridaben, pyridalyl, pyrifluquinazon, pyriprole, pyriproxyfen, pirimicarb, pyrimidifen, pirimiphos-methyl, pyrethrins, fipronil, fenazaquin, fenamiphos, bromopropylate, fenitrothion (MEP), fenoxycarb, fenothiocarb, phenothrin, fenobucarb, fensulfothion, fenthion (MPP), phenthoate (PAP), fenvalerate, fenpyroximate, fenpropathrin, fenbendazole, fosthiazate, formetanate, butathiofos, buprofezin, furathiocarb, prallethrin, fluacrypyrim, fluazinam, fluazuron, fluensulfone, flucycloxuron, flucythrinate, fluvalinate, flupyrazofos, flufenerim, flufenoxuron, flufenzine, flufenprox, fluproxyfen, flubrocythrinate, flubendiamide, flumethrin, flurimfen, prothiofos, protrifenbute, flonicamid, propaphos, propargite (BPPS), profenofos, profluthrin, propoxur (PHC), bromopropylate, beta-cyfluthrin, hexaflumuron, hexythiazox, heptenophos, permethrin, benclothiaz, bendiocarb, bensultap, benzoximate, benfuracarb, phoxim, phosalone, fosthiazate, fosthietan, phosphamidon, phosphocarb, phosmet (PMP), polynactins, formetanate, formothion, phorate, machine oil, malathion, milbemycin, milbemycin-A, milbemectin, mecarbam, mesulfenfos, methomyl, metaldehyde, metaflumizone, methamidophos, metam-ammonium, metam-sodium, methiocarb, methidathion (DMTP), methylisothiocyanate, methylneodecanamide, methylparathion, metoxadiazone, methoxychlor, methoxyfenozide, metofluthrin, methoprene, metolcarb, meperfluthrin, mevinphos, monocrotophos, monosultap, lambda-cyhalothrin, ryanodine, lufenuron, resmethrin, lepimectin, rotenone, levamisole hydrochloride, fenbutatin oxide, morantel tartarate, methyl bromide, tricyclohexyltin hydroxide (cyhexatin), calcium cyanamide, calcium polysulfide, sulfur and nicotine-sulfate.

Exemplary agricultural and horticultural microbicides used for the same purposes as above include aureofungin, azaconazole, azithiram, acypetacs, acibenzolar, acibenzolar-S-methyl, azoxystrobin, anilazine, amisulbrom, ampropylfos, ametoctradin, allyl alcohol, aldimorph, amobam, isotianil, isovaledione, isopyrazam, isoprothiolane, ipconazole, iprodione, iprovalicarb, iprobenfos, imazalil, iminoctadine, iminoctadine-albesilate, iminoctadine-triacetate, imibenconazole, uniconazole, uniconazole-P, echlomezole, edifenphos, etaconazole, ethaboxam, ethirimol, etem, ethoxyquin, etridiazole, enestroburin, epoxiconazole, oxadixyl, oxycarboxin, copper-8-quinolinolate, oxytetracycline, copper-oxinate, oxpoconazole, oxpoconazole-fumarate, oxolinic acid, octhilinone, ofurace, orysastrobin, metam-sodium, kasugamycin, carbamorph, carpropamid, carbendazim, carboxin, carvone, quinazamid, quinacetol, quinoxyfen, quinomethionate, captafol, captan, kiralaxyl, quinconazole, quintozene, guazatine, cufraneb, cuprobam, glyodin, griseofulvin, climbazole, cresol, kresoxim-methyl, chlozolinate, clotrimazole, chlobenthiazone, chloraniformethan, chloranil, chlorquinox, chloropicrin, chlorfenazole, chlorodinitronaphthalene, chlorothalonil, chloroneb, zarilamid, salicylanilide, cyazofamid, diethyl pyrocarbonate, diethofencarb, cyclafuramid, diclocymet, dichlozoline, diclobutrazol, dichlofluanid, cycloheximide, diclomezine, dicloran, dichlorophen, dichlone, disulfiram, ditalimfos, dithianon, diniconazole, diniconazole-M, zineb, dinocap, dinocton, dinosulfon, dinoterbon, dinobuton, dinopenton, dipyrithione, diphenylamine, difenoconazole, cyflufenamid, diflumetorim, cyproconazole, cyprodinil, cyprofuram, cypendazole, simeconazole, dimethirimol, dimethomorph, cymoxanil, dimoxystrobin, methyl bromide, ziram, silthiofam, streptomycin, spiroxamine, sultropen, sedaxane, zoxamide, dazomet, thiadiazin, tiadinil, thiadifluor, thiabendazole, tioxymid, thiochlorfenphim, thiophanate, thiophanate-methyl, thicyofen, thioquinox, chinomethionat, thifluzamide, thiram, decafentin, tecnazene, tecloftalam, tecoram, tetraconazole, debacarb, dehydroacetic acid, tebuconazole, tebufloquin, dodicin, dodine, dodecyl benzensulfonate bis-ethylene diamine copper(II) (DBEDC), dodemorph, drazoxolon, triadimenol, triadimefon, triazbutil, triazoxide, triamiphos, triarimol, trichlamide, tricyclazole, triticonazole, tridemorph, tributyltin oxide, triflumizole, trifloxystrobin, triforine, tolylfluanid, tolclofos-methyl, natamycin, nabam, nitrothal-isopropyl, nitrostyrene, nuarimol, copper nonylphenol sulfonate, halacrinate, validamycin, valifenalate, harpin protein, bixafen, picoxystrobin, picobenzamide, bithionol, bitertanol, hydroxyisoxazole, hydroxyisoxazole-potassium, binapacryl, biphenyl, piperalin, hymexazol, pyraoxystrobin, pyracarbolid, pyraclostrobin, pyrazophos, pyrametostrobin, pyriofenone, pyridinitril, pyrifenox, pyribencarb, pyrimethanil, pyroxychlor, pyroxyfur, pyroquilon, vinclozolin, famoxadone, fenapanil, fenamidone, fenaminosulf, fenarimol, fenitropan, fenoxanil, ferimzone, ferbam, fentin, fenpiclonil, fenpyrazamine, fenbuconazole, fenfuram, fenpropidin, fenpropimorph, fenhexamid, phthalide, buthiobate, butylamine, bupirimate, fuberidazole, blasticidin-S, furametpyr, furalaxyl, fluacrypyrim, fluazinam, fluoxastrobin, fluotrimazole, fluopicolide, fluopyram, fluoroimide, furcarbanil, fluxapyroxad, fluquinconazole, furconazole, furconazole-cis, fludioxonil, flusilazole, flusulfamide, flutianil, flutolanil, flutriafol, furfural, furmecyclox, flumetover, flumorph, proquinazid, prochloraz, procymidone, prothiocarb, prothioconazole, propamocarb, propiconazole, propineb, furophanate, probenazole, bromuconazole, hexachlorobutadiene, hexaconazole, hexylthiofos, bethoxazin, benalaxyl, benalaxyl-M, benodanil, benomyl, pefurazoate, benquinox, penconazole, benzamorf, pencycuron, benzohydroxamic acid, bentaluron, benthiazole, benthiavalicarb-isopropyl, penthiopyrad, penflufen, boscalid, phosdiphen, fosetyl, fosetyl-Al, polyoxins, polyoxorim, polycarbamate, folpet, formaldehyde, machine oil, maneb, mancozeb, mandipropamid, myclozolin, myclobutanil, mildiomycin, milneb, mecarbinzid, methasulfocarb, metazoxolon, metam, metam-sodium, metalaxyl, metalaxyl-M, metiram, methyl isothiocyanate, meptyldinocap, metconazole, metsulfovax, methfuroxam, metominostrobin, metrafenone, mepanipyrim, mefenoxam, meptyldinocap, mepronil, mebenil, iodomethane, rabenzazole, benzalkonium chloride, basic copper chloride, basic copper sulfate, inorganic microbicides such as silver, sodium hypochlorite, cupric hydroxide, wettable sulfur, calcium polysulfide, potassium hydrogen carbonate, sodium hydrogen carbonate, sulfur, copper sulfate anhydride, nickel dimethyldithiocarbamate, copper compounds such as copper-8-quinolinolate (oxine copper), zinc sulfate and copper sulfate pentahydrate.

Exemplary herbicides used for the same purposes as above include 1-naphthylacetamide, 2,4-PA, 2,3,6-TBA, 2,4,5-T, 2,4,5-TB, 2,4-D, 2,4-DB, 2,4-DEB, 2,4-DEP, 3,4-DA, 3,4-DB, 3,4-DP, 4-CPA, 4-CPB, 4-CPP, MCP, MCPA, MCPA-thioethyl, MCPB, ioxynil, aclonifen, azafenidin, acifluorfen, aziprotryne, azimsulfuron, asulam, acetochlor, atrazine, atraton, anisuron, anilofos, aviglycine, abscisic acid, amicarbazone, amidosulfuron, amitrole, aminocyclopyrachlor, aminopyralid, amibuzin, amiprophos-methyl, ametridione, ametryn, alachlor, allidochlor, alloxydim, alorac, isouron, isocarbamid, isoxachlortole, isoxapyrifop, isoxaflutole, isoxaben, isocil, isonoruron, isoproturon, isopropalin, isopolinate, isomethiozin, inabenfide, ipazine, ipfencarbazone, iprymidam, imazaquin, imazapic, imazapyr, imazamethapyr, imazamethabenz, imazamethabenz-methyl, imazamox, imazethapyr, imazosulfuron, indaziflam, indanofan, indolebutyric acid, uniconazole-P, eglinazine, esprocarb, ethametsulfuron, ethametsulfuron-methyl, ethalflulin, ethiolate, ethychlozate-ethyl, ethidimuron, etinofen, ethephon, ethoxysulfuron, ethoxyfen, etnipromid, ethofumesate, etobenzanid, epronaz, erbon, endothal, oxadiazon, oxadiargyl, oxaziclomefone, oxasulfuron, oxapyrazon, oxyfluorfen, oryzalin, orthosulfamuron, orbencarb, cafenstrole, cambendichlor, carbasulam, carfentrazone, carfentrazone-ethyl, karbutilate, carbetamide, carboxazole, quizalofop, quizalofop-P, quizalofop-ethyl, xylachlor, quinoclamine, quinonamid, quinclorac, quinmerac, cumyluron, cliodinate, glyphosate, glufosinate, glufosinate-P, credazine, clethodim, cloxyfonac, clodinafop, clodinafop-propargyl, chlorotoluron, clopyralid, cloproxydim, cloprop, chlorbromuron, clofop, clomazone, chlomethoxynil, chlomethoxyfen, clomeprop, chlorazifop, chlorazine, cloransulam, chloranocryl, chloramben, cloransulam-methyl, chloridazon, chlorimuron, chlorimuron-ethyl, chlorsulfuron, chlorthal, chlorthiamid, chlortoluron, chlornitrofen, chlorfenac, chlorfenprop, chlorbufam, chlorflurazole, chlorflurenol, chlorprocarb, chlorpropham, chlormequat, chloreturon, chloroxynil, chloroxuron, chloropon, saflufenacil, cyanazine, cyanatryn, di-allate, diuron, diethamquat, dicamba, cycluron, cycloate, cycloxydim, diclosulam, cyclosulfamuron, dichlorprop, dichlorprop-P, dichlobenil, diclofop, diclofop-methyl, dichlormate, dichloralurea, diquat, cisanilide, disul, siduron, dithiopyr, dinitramine, cinidon-ethyl, dinosam, cinosulfuron, dinoseb, dinoterb, dinofenate, dinoprop, cyhalofop-butyl, diphenamid, difenoxuron, difenopenten, difenzoquat, cybutryne, cyprazine, cyprazole, diflufenican, diflufenzopyr, dipropetryn, cypromid, cyperquat, gibberellin, simazine, dimexano, dimethachlor, dimidazon, dimethametryn, dimethenamid, simetryn, simeton, dimepiperate, dimefuron, cinmethylin, swep, sulglycapin, sulcotrione, sulfallate, sulfentrazone, sulfosulfuron, sulfometuron, sulfometuron-methyl, secbumeton, sethoxydim, sebuthylazine, terbacil, daimuron, dazomet, dalapon, thiazafluron, thiazopyr, thiencarbazone, thiencarbazone-methyl, tiocarbazil, tioclorim, thiobencarb, thidiazimin, thidiazuron, thifensulfuron, thifensulfuron-methyl, desmedipham, desmetryn, tetrafluron, thenylchlor, tebutam, tebuthiuron, terbumeton, tepraloxydim, tefuryltrione, tembotrione, delachlor, terbacil, terbucarb, terbuchlor, terbuthylazine, terbutryn, topramezone, tralkoxydim, triaziflam, triasulfuron, tri-allate, trietazine, tricamba, triclopyr, tridiphane, tritac, tritosulfuron, triflusulfuron, triflusulfuron-methyl, trifluralin, trifloxysulfuron, tripropindan, tribenuron-methyl, tribenuron, trifop, trifopsime, trimeturon, naptalam, naproanilide, napropamide, nicosulfuron, nitralin, nitrofen, nitrofluorfen, nipyraclofen, neburon, norflurazon, noruron, barban, paclobutrazol, paraquat, parafluron, haloxydine, haloxyfop, haloxyfop-P, haloxyfop-methyl, halosafen, halosulfuron, halosulfuron-methyl, picloram, picolinafen, bicyclopyrone, bispyribac, bispyribac-sodium, pydanon, pinoxaden, bifenox, piperophos, hymexazol, pyraclonil, pyrasulfotole, pyrazoxyfen, pyrazosulfuron, pyrazosulfuron-ethyl, pyrazolate, bilanafos, pyraflufen-ethyl, pyriclor, pyridafol, pyrithiobac, pyrithiobac-sodium, pyridate, pyriftalid, pyributicarb, pyribenzoxim, pyrimisulfan, primisulfuron, pyriminobac-methyl, pyroxasulfone, pyroxsulam, fenasulam, phenisopham, fenuron, fenoxasulfone, fenoxaprop, fenoxaprop-P, fenoxaprop-ethyl, phenothiol, fenoprop, phenobenzuron, fenthiaprop, fenterecol, fentrazamide, phenmedipham, phenmedipham-ethyl, butachlor, butafenacil, butamifos, buthiuron, buthidazole, butylate, buturon, butenachlor, butroxydim, butralin, flazasulfuron, flamprop, furyloxyfen, prynachlor, primisulfuron-methyl, fluazifop, fluazifop-P, fluazifop-butyl, fluazolate, fluroxypyr, fluothiuron, fluometuron, fluoroglycofen, flurochloridone, fluorodifen, fluoronitrofen, fluoromidine, flucarbazone, flucarbazone-sodium, fluchloralin, flucetosulfuron, fluthiacet, fluthiacet-methyl, flupyrsulfuron, flufenacet, flufenican, flufenpyr, flupropacil, flupropanate, flupoxam, flumioxazin, flumiclorac, flumiclorac-pentyl, flumipropyn, flumezin, fluometuron, flumetsulam, fluridone, flurtamone, fluroxypyr, pretilachlor, proxan, proglinazine, procyazine, prodiamine, prosulfalin, prosulfuron, prosulfocarb, propaquizafop, propachlor, propazine, propanil, propyzamide, propisochlor, prohydrojasmon, propyrisulfuron, propham, profluazol, profluralin, prohexadione-calcium, propoxycarbazone, propoxycarbazone-sodium, profoxydim, bromacil, brompyrazon, prometryn, prometon, bromoxynil, bromofenoxim, bromobutide, bromobonil, florasulam, hexachloroacetone, hexazinone, pethoxamid, benazolin, penoxsulam, pebulate, beflubutamid, vernolate, perfluidone, bencarbazone, benzadox, benzipram, benzylaminopurine, benzthiazuron, benzfendizone, bensulide, bensulfuron-methyl, benzoylprop, benzobicyclon, benzofenap, benzofluor, bentazone, pentanochlor, benthiocarb, pendimethalin, pentoxazone, benfluralin, benfuresate, fosamine, fomesafen, foramsulfuron, forchlorfenuron, maleic hydrazide, mecoprop, mecoprop-P, medinoterb, mesosulfuron, mesosulfuron-methyl, mesotrione, mesoprazine, methoprotryne, metazachlor, methazole, metazosulfuron, methabenzthiazuron, metamitron, metamifop, metam, methalpropalin, methiuron, methiozolin, methiobencarb, methyldymron, metoxuron, metosulam, metsulfuron, metsulfuron-methyl, metflurazon, metobromuron, metobenzuron, methometon, metolachlor, metribuzin, mepiquat-chloride, mefenacet, mefluidide, monalide, monisouron, monuron, monochloroacetic acid, monolinuron, molinate, morfamquat, iodosulfuron, iodosulfuron-methyl-sodium, iodobonil, iodomethane, lactofen, linuron, rimsulfuron, lenacil, rhodethanil, calcium peroxide and methyl bromide.

Exemplary biopesticides used for the same purposes as above include viral formulations such as nuclear polyhedrosis viruses (NPV), granulosis viruses (GV), cytoplasmic polyhedrosis viruses (CPV) and entomopox viruses (EPV); microbial pesticides used as an insecticide or a nematicide, such as Monacrosporium phymatophagum, Steinernema carpocapsae, Steinernema kushidai and Pasteuria *penetrans*; microbial pesticides used as a microbicide, such as *Trichoderma* lignorum, *Agrobacterium* radiobactor, avirulent *Erwinia carotovora* and *Bacillus subtilis*; and biopesticides used as a herbicide, such as *Xanthomonas campestris*. Such a combined use of the agricultural and horticultural insecticide of the present invention with the foregoing biopesticide as a mixture can be expected to provide the same effect as above.

Other examples of the biopesticides include natural predators such as *Encarsia formosa, Aphidius colemani, Aphidoletes aphidimyza, Diglyphus isaea, Dacnusa sibirica, Phytoseiulus persimilis, Amblyseius cucumeris* and *Orius sauteri*; microbial pesticides such as *Beauveria brongniartii*; and pheromones such as (Z)-10-tetradecenyl acetate, (E,Z)-4,10-tetradecadienyl acetate, (Z)-8-dodecenyl acetate, (Z)-11-tetradecenyl acetate, (Z)-13-icosen-10-one and 14-methyl-1-octadecene.

The compound of the present invention or a salt thereof is also suitable for the disinfection of parasites that live in the interior of or on the exterior of animals such as humans, domestic animals and pets.

The present invention also includes an animal ectoparasite control agent comprising the compound of the present invention or a salt thereof as an active ingredient; and a method for controlling animal ectoparasites, comprising treating animal ectoparasites with the animal ectoparasite control agent. The compound of the present invention can be used by spot-on or pour-on application usually to one site or two sites on the skin of an animal such as a cat or a dog. The application area is usually 5 to 10 cm$^2$. Once applied, the compound of the present invention preferably diffuses throughout the animal's body and then dries without crystallization or changes in visual appearance or texture. The preferable amount of the compound used is selected from the range of 0.1 to 10 mL according to the weight of the animal, and in particular, is about 0.5 to 1 mL for a cat and about 0.3 to 3 mL for a dog.

The ectoparasite control agent of the present invention is effective against, for example, the following animal ectoparasites. Siphonaptera parasites include the species of the genus *Pulex* such as *Pulex irritans*; the species of the genus *Ctenocephalides* such as *Ctenocephalides felis* and *Ctenocephalides canis*; the species of the genus *Xenopsylla* such as *Xenopsylla cheopis*; the species of the genus *Tunga* such as *Tunga penetrans*; the species of the genus *Echidnophaga* such as *Echidnophaga gallinacea*; and the species of the genus *Nosopsyllus* such as *Nosopsyllus fasciatus*.

Siphunculata parasites include the species of the genus *Pediculus* such as *Pediculus humanus* capitis; the species of the genus *Pthirus* such as *Pthirus pubis*; the species of the genus *Haematopinus* such as *Haematopinus eurysternus* and *Haematopinus suis*; the species of the genus *Damalinia* such as *Damalinia ovis* and *Damalinia bovis*; the species of the genus *Linognathus* such as *Linognathus vituli* and *Linognathus ovillus* (parasitic on the trunk of a sheep's body); and the species of the genus *Solenopotes* such as *Solenopotes capillatus*.

Mallophaga parasites include the species of the genus *Menopon* such as *Menopon gallinae*; Trimenopon spp.; Trinoton spp.; the species of the genus *Trichodectes* such as *Trichodectes canis*; the species of the genus *Felicola* such as *Felicola subrostratus*; the species of the genus *Bovicola* such as *Bovicola bovis*; the species of the genus *Menacanthus* such as *Menacanthus stramineus; Werneckiella* spp.; and *Lepikentron* spp.

Hemiptera parasites include the species of the genus *Cimex* such as *Cimex lectularius* and *Cimex hemipterus*; the species of the genus *Reduvius* such as *Reduvius senilis*; the species of the genus *Arilus* such as *Arilus critatus*; the species of the genus *Rhodnius* such as *Rhodnius prolixus*; the species of the genus *Triatoma* such as *Triatoma rubrofasciata*; and *Panstrongylus* spp.

Acarina parasites include the species of the genus *Amblyomma* such as *Amblyomma americanum* and *Amblyomma maculatum*; the species of the genus *Boophilus* such as *Boophilus microplus* and *Boophilus annulatus*; the species of the genus *Dermacentor* such as *Dermacentor variabilis, Dermacentor taiwanicus* and *Dermacentor andersoni*; the species of the genus *Haemaphysalis* such as *Haemaphysalis longicornis, Haemaphysalis flava* and *Haemaphysalis campanulata*; the species of the genus *Ixodes* such as *Ixodes ovatus, Ixodes persulcatus, Ixodes scapularis, Ixodes pacificus* and *Ixodes holocyclus*; the species of the genus *Rhipicephalus* such as *Rhipicephalus sanguineus* and *Rhipicephalus appendiculatus*; the species of the genus *Argas* such as *Argas persicus*; the species of the genus *Ornithodoros* such as *Ornithodoros hermsi* and *Ornithodoros turicata*; the species of the genus *Psoroptes* such as *Psoroptes ovis* and *Psoroptes equi*; the species of the genus *Knemidocoptes* such as *Knemidocoptes mutans*; the species of the genus *Notoedres* such as *Notoedres cati* and *Notoedres muris*; the species of the genus *Sarcoptes* such as *Sarcoptes scabiei*; the species of the genus *Otodectes* such as *Otodectes cynotis*; the species of the genus *Listrophorus* such as *Listrophorus gibbus; Chorioptes* spp.; *Hypodectes* spp.; *Pterolichus* spp.; *Cytodites* spp.; *Laminosioptes* spp.; the species of the genus *Dermanyssus* such as *Dermanyssus gallinae*; the species of the genus *Ornithonyssus* such as *Ornithonyssus sylviarum* and *Ornithonyssus bacoti*; the species of the genus *Varroa* such as *Varroa jacobsoni*; the species of the genus *Cheyletiella* such as *Cheyletiella yasguri* and *Cheyletiella blakei; Ornithocheyletia* spp.; the species of the genus *Demodex* such as *Demodex canis* and *Demodex cati; Myobia* spp.; *Psorergates* spp.; and the species of the genus *Trombicula* such as *Trombicula akamushi, Trombicula pallida* and *Trombicula scutellaris*. Preferred are Siphonaptera parasites, Siphunculata parasites and Acarina parasites.

The animals to which the ectoparasite control agent of the present invention is administrable can be host animals for the above-mentioned animal ectoparasites. Such animals are usually homeotherms and poikilotherms which are bred as domestic animals or pets. Such homeotherms include mammals such as cattle, buffalos, sheep, goats, pigs, camels, deer, fallow deer, reindeer, horses, donkeys, dogs, cats, rabbits, ferrets, mice, rats, hamsters, squirrels and monkeys; fur-bearing animals such as minks, chinchillas and raccoons; and birds such as chickens, geese, turkeys, domestic ducks, pigeons, parrots and quails. The above-mentioned poikilotherms include reptiles such as tortoises, sea turtles, pond sliders, Japanese pond turtles, lizards, iguanas, chameleons, geckos, pythons, colubrid snakes and cobras. Preferred are homeotherms, and more preferred are mammals such as dogs, cats, cattle, horses, pigs, sheep and goats.

Hereinafter, the production examples of representative compounds of the present invention and their intermediates will be described in more detail, but the present invention is not limited only to these examples.

EXAMPLES

Example 1-1

Production of 3-(ethylsulfonyl)-2-(3-methyl-6-(trifluoromethyl)-3H-imidazo[4,5-b]pyridin-2-yl)-6-vinylquinoline

[Chem. 10]

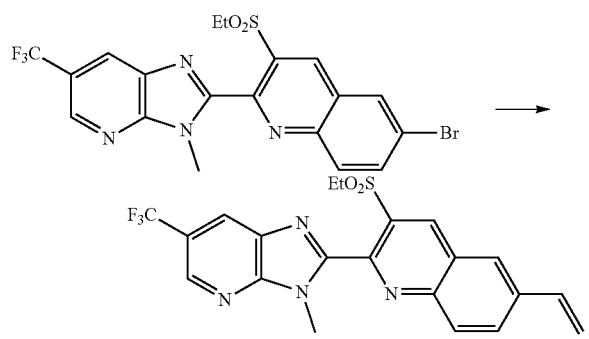

To 6-bromo-3-ethylsulfonyl-2-(3-methyl-6-(trifluoromethyl)-3H-imidazo[4,5-b]pyridin-2-yl)quinoline (200 mg, 0.40 mmol), which was produced by the production method described in WO 2016/091731, toluene (9 mL), water (2 mL), potassium vinyltrifluoroborate (107 mg, 0.80 mmol), a complex of [1,1'-bis(diphenylphosphino) ferrocene]dichloropalladium with acetone (61 mg, 0.08 mmol) and potassium phosphate (170 mg, 0.80 mmol) were added, and the mixture was stirred at 90° C. for 3 hours. To the reaction mixture, silica gel was added, and silica gel column chromatography was performed to give the desired compound (119 mg, 67%).

Melting point: 97 to 98° C.

Example 1-2

Production of 3-(ethylsulfonyl)-2-(3-methyl-6-(trifluoromethyl)-3H-imidazo[4,5-b]pyridin-2-yl)quinoline-6-carbaldehyde

[Chem. 11]

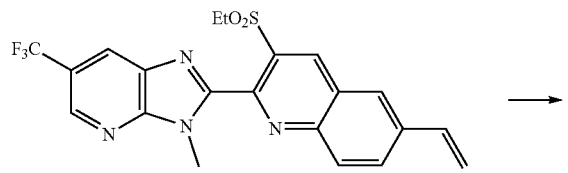

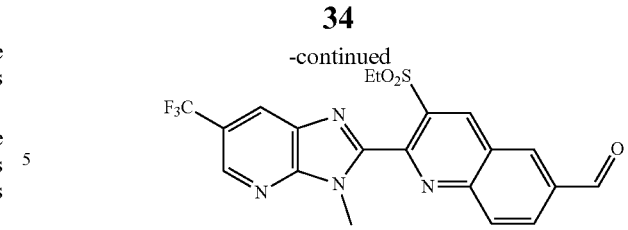

To 3-(ethylsulfonyl)-2-(3-methyl-6-(trifluoromethyl)-3H-imidazo[4,5-b]pyridin-2-yl)-6-vinylquinoline (43 mg, 0.10 mmol), THF (tetrahydrofuran) (0.6 mL), water (0.3 mL), N-methylmorpholine oxide (70 mg, 0.60 mmol) and osmium tetroxide (0.04 M solution in t-BuOH, 0.2 mL, 0.06 mmol) were added, and the mixture was stirred at room temperature for 2 hours. After the successful progress of the reaction was confirmed by TLC, sodium periodate (26 mg, 0.12 mmol) was added, and the mixture was stirred at room temperature for 2 hours. After the completion of the reaction, an aqueous sodium thiosulfate solution was added, and ethyl acetate extraction was performed. The organic layer was washed with a saturated aqueous sodium chloride solution. The washed organic layer was dried over anhydrous sodium sulfate, and the solvent was evaporated off in vacuo. The residue was subjected to silica gel column chromatography to give the desired compound (22 mg, 49%).

Melting point: 205 to 206° C.

Example 1

Production of (E)-3-(ethylsulfonyl)-2-(3-methyl-6-(trifluoromethyl)-3H-imidazo[4,5-b]pyridin-2-yl)quinoline-6-carbaldehyde oxime (Compound Number 1-1)

[Chem. 12]

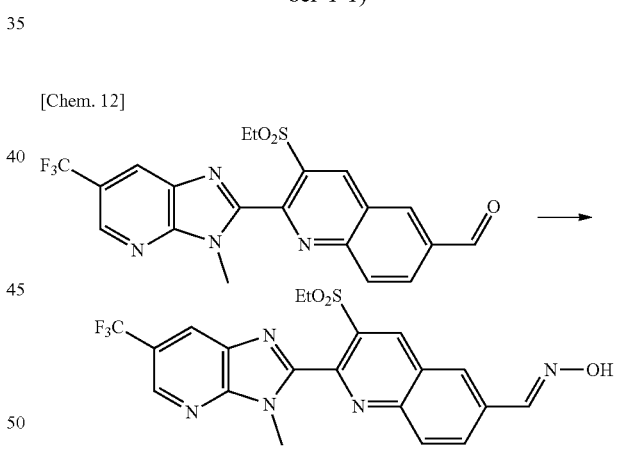

To 3-(ethylsulfonyl)-2-(3-methyl-6-(trifluoromethyl)-3H-imidazo[4,5-b]pyridin-2-yl)quinoline-6-carbaldehyde (22 mg, 0.05 mmol), ethanol (0.6 mL), hydroxy amine hydrochloride (5 mg, 0.07 mmol) and sodium acetate (6 mg, 0.07 mmol) were added, and the mixture was heated under reflux with stirring for 2 hours. After the completion of the reaction, an aqueous ammonium chloride solution was added, and ethyl acetate extraction was performed. The organic layer was washed with a saturated aqueous sodium chloride solution. The washed organic layer was dried over anhydrous sodium sulfate, and the solvent was evaporated off in vacuo. The residue was subjected to silica gel column chromatography to give the desired compound (21 mg, 95%).

Melting point: 123 to 124° C.

Example 2

Production of (E)-3-(ethylsulfonyl)-2-(3-methyl-6-(trifluoromethyl)-3H-imidazo[4,5-b]pyridin-2-yl)quinoline-6-carbaldehyde O-(2,2,2-trifluoroethyl) oxime (Compound Number 1-7)

[Chem. 13]

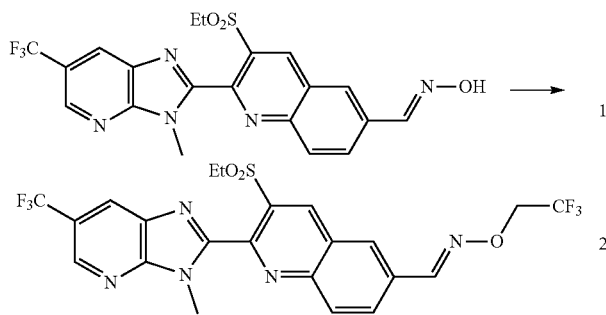

To (E)-3-(ethylsulfonyl)-2-(3-methyl-6-(trifluoromethyl)-3H-imidazo[4,5-b]pyridin-2-yl)quinoline-6-carbaldehyde oxime (21 mg, 0.05 mmol), DMF (dimethylformamide) (0.3 mL), cesium carbonate (32 mg, 0.10 mmol) and 2,2,2-trifluoroethyl trifluoromethanesulfonate (22 mg, 0.10 mmol) were added, and the mixture was stirred at room temperature for 2 hours. After the completion of the reaction, water was added, and ethyl acetate extraction was performed. The organic layer was washed with a saturated aqueous sodium chloride solution. The washed organic layer was dried over anhydrous sodium sulfate, and the solvent was evaporated off in vacuo. The residue was subjected to column chromatography to give the desired compound (22 mg, 85%).

Melting point: 92 to 93° C.

Example 3-1

Production of 1-(3-(ethylsulfonyl)-2-(5-(trifluoromethylthio)benzo[d]oxazol-2-yl)quinolin-6-yl)ethanone

[Chem. 14]

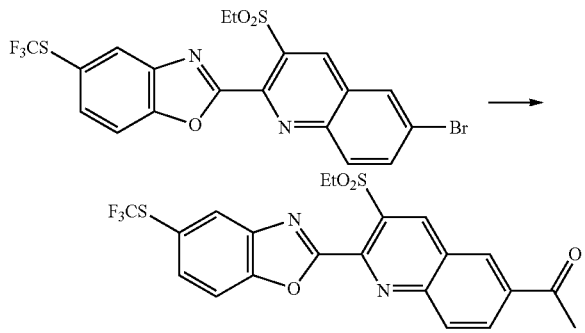

To a DMF solution (6 mL) of 6-bromo-3-ethylsulfonyl-2-(5-(trifluoromethylthio)benzo[d]oxazol-2-yl)quinoline (284 mg, 0.55 mmol), which was produced by the production method described in WO 2016/091731, tetrakis(triphenylphosphine)palladium (64 mg, 0.055 mmol) and tributyl(1-ethoxyvinyl)tin (260 mg, 0.72 mmol) were added, and the mixture was stirred at 80° C. for 3 hours. The reaction mixture was allowed to cool down to room temperature. To this, 1 M HCl (6 mL) was added, and the mixture was stirred for 2 hours. After the completion of the reaction, a saturated aqueous sodium hydrogen carbonate solution was added, and ethyl acetate extraction was performed. The organic layer was washed with a saturated aqueous sodium chloride solution. The washed organic layer was dried over anhydrous magnesium sulfate, and the solvent was evaporated off in vacuo. The residue was subjected to silica gel column chromatography to give the desired compound (263 mg, 99%).

Melting point: 218 to 219° C.

Example 3

Production of 1-(3-(ethylsulfonyl)-2-(5-(trifluoromethylthio)benzo[d]oxazol-2-yl)quinolin-6-yl)ethanone oxime (Compound Number 3-2)

[Chem. 15]

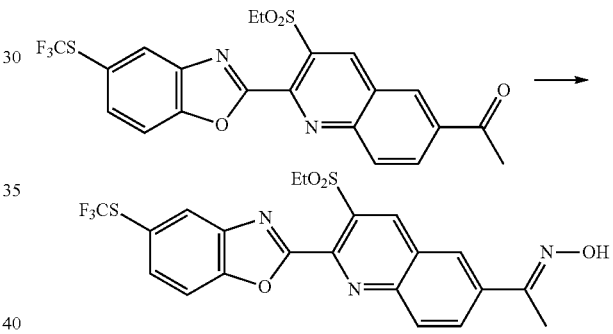

Following the production method as described in Example 1, the desired compound (108 mg, 99%) was produced from 1-(3-(ethylsulfonyl)-2-(5-(trifluoromethylthio)benzo[d]oxazol-2-yl)quinolin-6-yl)ethanone (101 mg, 0.22 mmol).

Melting point: 246 to 247° C.

Example 4

Production of 1-(3-(ethylsulfonyl)-2-(5-(trifluoromethylthio)benzo[d]oxazol-2-yl)quinolin-6-yl)ethanone O-(2,2,2-trifluoroethyl)oxime (Compound Number 3-8)

[Chem. 16]

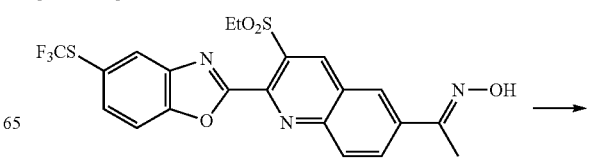

37

-continued

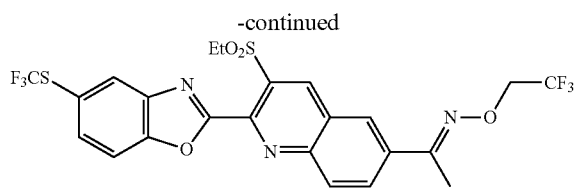

Following the production method as described in Example 2, the desired compound (83 mg, 75%) was produced from 1-(3-(ethylsulfonyl)-2-(5-(trifluoromethylthio)benzo[d]oxazol-2-yl) quinolin-6-yl)ethanone oxime (98 mg, 0.20 mmol).

Melting point: 216 to 217° C.

Production Example 5

Production Method of 3-(ethylsulfonyl)-2-(3-methyl-6-(trifluoromethyl)-3H-imidazo[4,5-b]pyridin-2-yl)quinoline-7-carbaldehyde O-(methylthiomethyl)oxime (Compound Number 2-19)

[Chem. 17]

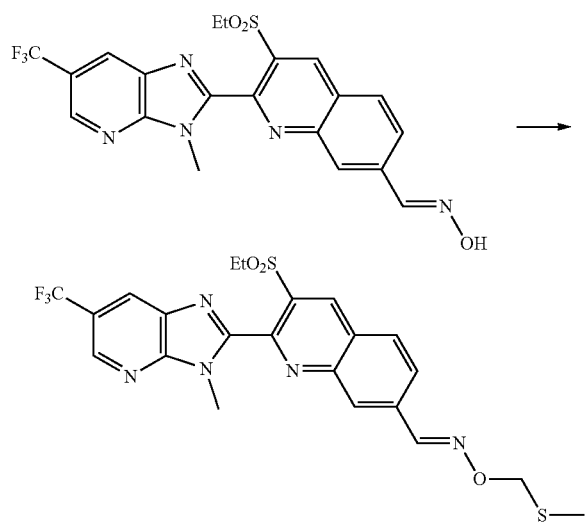

To 3-(ethylsulfonyl)-2-(3-methyl-6-(trifluoromethyl)-3H-imidazo[4,5-b]pyridin-2-yl)quinoline-7-carbaldehyde oxime (160 mg, 0.34 mmol), DMF (1.8 mL), cesium carbonate (222 mg, 0.68 mmol) and chloromethyl methylsulfide (66 mg, 0.68 mmol) were added, and the mixture was allowed to react at room temperature for 1.5 hours. After the completion of the reaction, water was added, and ethyl acetate extraction was performed. The organic layer was washed with a saturated aqueous sodium chloride solution. The washed organic layer was dried over anhydrous sodium sulfate, and the solvent was evaporated off in vacuo. The residue was subjected to column chromatography to give the desired compound.

Yield: 119 mg

Percent yield: 66%

Melting point: 70 to 71° C.

38

Production Example 6

Production Method of 3-(ethylsulfonyl)-2-(3-methyl-6-(trifluoromethyl)-3H-imidazo[4,5-b]pyridin-2-yl)quinoline-7-carbaldehyde O-(methylsulfinylmethyl)oxime (Compound Number 2-24)

[Chem. 18]

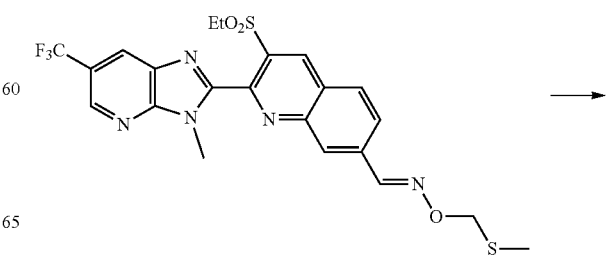

3-(Ethylsulfonyl)-2-(3-methyl-6-(trifluoromethyl)-3H-imidazo[4,5-b]pyridin-2-yl)quinoline-7-carbaldehyde O-(methylthiomethyl)oxime (41 mg, 0.077 mmol) was dissolved in ethyl acetate (0.8 mL). To this, m-CPBA (m-chloroperoxybenzoic acid)(ca. 65%, 21 mg, 0.077 mmol) was added, and the mixture was stirred at room temperature for 2 hours. After the completion of the reaction, an aqueous sodium thiosulfate solution was added, and ethyl acetate extraction was performed. The organic layer was washed with a saturated aqueous sodium bicarbonate solution and a saturated aqueous sodium chloride solution. The washed organic layer was dried over anhydrous sodium sulfate, and the solvent was evaporated off in vacuo. The residue was subjected to silica gel column chromatography to give the desired compound.

Yield: 28 mg

Percent yield: 67%

Melting point: 163 to 164° C.

Production Example 7

Production Method of 3-(ethylsulfonyl)-2-(3-methyl-6-(trifluoromethyl)-3H-imidazo[4,5-b]pyridin-2-yl)quinoline-7-carbaldehyde O-(methylsulfonylmethyl)oxime (Compound Number 2-25)

[Chem. 19]

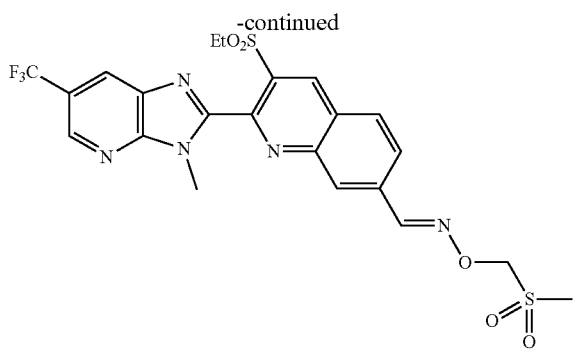

3-(Ethylsulfonyl)-2-(3-methyl-6-(trifluoromethyl)-3H-imidazo[4,5-b]pyridin-2-yl)quinoline-7-carbaldehyde O-(methylthiomethyl)oxime (40 mg, 0.077 mmol) was dissolved in ethyl acetate (0.8 mL). To this, m-CPBA (ca. 65%, 45 mg, 0.17 mmol) was added, and the mixture was stirred at room temperature for 2 hours. After the completion of the reaction, an aqueous sodium thiosulfate solution was added, and ethyl acetate extraction was performed. The organic layer was washed with a saturated aqueous sodium bicarbonate solution and a saturated aqueous sodium chloride solution. The washed organic layer was dried over anhydrous sodium sulfate, and the solvent was evaporated off in vacuo. The residue was subjected to silica gel column chromatography to give 3-(ethylsulfonyl)-2-(3-methyl-6-(trifluoromethyl)-3H-imidazo[4,5-b]pyridin-2-yl)quinoline-7-carbaldehyde O-(methylsulfonylmethyl)oxime.

Yield: 35 mg
Percent yield: 82%
Melting point: 74 to 75° C.

Hereinafter, formulation examples are shown, but the present invention is not limited thereto. In the formulation examples, "part" means part by weight.

Formulation Example 1

| Compound of the present invention | 10 parts |
| Xylene | 70 parts |
| N-methylpyrrolidone | 10 parts |
| Mixture of polyoxyethylene nonylphenyl ether and calcium alkylbenzene sulfonate | 10 parts |

The above ingredients are uniformly mixed for dissolution to give an emulsifiable concentrate formulation.

Formulation Example 2

| Compound of the present invention | 3 parts |
| Clay powder | 82 parts |
| Diatomite powder | 15 parts |

The above ingredients are uniformly mixed and then pulverized to give a dust formulation.

Formulation Example 3

| Compound of the present invention | 5 parts |
| Mixture of bentonite powder and clay powder | 90 parts |
| Calcium lignosulfonate | 5 parts |

The above ingredients are uniformly mixed. After addition of an appropriate volume of water, the mixture is kneaded, granulated and dried to give a granular formulation.

Formulation Example 4

| Compound of the present invention | 20 parts |
| Kaolin and synthetic high-dispersion silicic acid | 75 parts |
| Mixture of polyoxyethylene nonylphenyl ether and calcium alkylbenzene sulfonate | 5 parts |

The above ingredients are uniformly mixed and then pulverized to give a wettable powder formulation.

Hereinafter, test examples in connection with the present invention are shown, but the present invention is not limited thereto.

Test Example 1

Test for Control Efficacy on *Myzus persicae*

Chinese cabbage plants were planted in plastic pots (diameter: 8 cm, height: 8 cm), Green peach aphids (*Myzus persicae*) were propagated on the plants, and the number of surviving Green peach aphids in each pot was counted. The oxime group-containing quinoline compounds represented by the general formula (1) of the present invention or salts thereof were separately dispersed in water and diluted to 500 ppm. The agrochemical dispersions were applied to the foliage of the potted Chinese cabbage plants. After the plants were air-dried, the pots were kept in a greenhouse. At 6 days after the foliar application, the number of surviving Green peach aphids on the Chinese cabbage plant in each pot was counted, the control rate was calculated according to the formula shown below, and the control efficacy was evaluated according to the criteria shown below.

$$\text{Control rate} = 100 - \{(T \times Ca)/(Ta \times C)\} \times 100 \quad [\text{Math. 1}]$$

Ta: the number of survivors before the foliar application in a treatment plot
T: the number of survivors after the foliar application in a treatment plot
Ca: the number of survivors before the foliar application in a non-treatment plot
C: the number of survivors after the foliar application in a non-treatment plot
Criteria
A: the control rate is 100%.
B: the control rate is 90 to 99%.
C: the control rate is 80 to 89%.
D: the control rate is 50 to 79%.

As a result, the compounds 1-1, 1-7, 2-1, 2-2, 2-3, 2-5, 2-7, 2-8, 2-11, 2-13, 2-19, 2-21, 2-22, 2-23, 2-24, 2-25, 2-26, 2-27, 2-28, 2-29, 2-31, 2-32, 2-33, 2-34, 2-35, 2-36, 2-37, 2-38, 2-39, 3-1, 3-2, 3-8, 3-21, 3-23, 3-27, 3-33, 4-21, 4-25, 4-27, 4-39, 4-41, 5-1, 5-2, 5-3, 5-4, 5-5, 5-6, 5-7, 5-8, 6-1, 6-2, 6-3, 6-4, 6-5, 6-6, 6-7, 6-8, 6-9, 6-10 and 6-11 of the present invention showed the activity level evaluated as A.

Test Example 2

Insecticidal Test on *Laodelphax striatellus*

The oxime group-containing quinoline compounds represented by the general formula (1) of the present invention or salts thereof were separately dispersed in water and diluted to 500 ppm. Rice plant seedlings (variety: Nihonbare) were dipped in the agrochemical dispersions for 30 seconds. After air-dried, each seedling was put into a separate glass test tube and inoculated with ten 3rd-instar larvae of *Laodelphax striatellus*, and then the glass test tubes were capped with cotton plugs. At 8 days after the inoculation, the numbers of surviving larvae and dead larvae were counted, the corrected mortality rate was calculated according to the formula shown below, and the insecticidal efficacy was evaluated according to the criteria shown below.

Corrected mortality rate (%)=100×(Survival rate in a non-treatment plot−Survival rate in a treatment plot)/Survival rate in a non-treatment plot [Math. 2]

Criteria
A: the corrected mortality rate is 100%.
B: the corrected mortality rate is 90 to 99%.
C: the corrected mortality rate is 80 to 89%.
D: the corrected mortality rate is 50 to 79%.

As a result, the compounds 1-1, 1-7, 2-1, 2-2, 2-3, 2-5, 2-7, 2-8, 2-11, 2-13, 2-19, 2-21, 2-22, 2-23, 2-24, 2-25, 2-26, 2-27, 2-28, 2-29, 2-31, 2-32, 2-33, 2-34, 2-35, 2-36, 2-37, 2-38, 2-39, 3-1, 3-2, 3-8, 3-21, 3-23, 3-27, 3-33, 4-21, 4-25, 4-27, 4-39, 4-41, 5-1, 5-2, 5-3, 5-4, 5-5, 5-6, 5-7, 5-8, 6-1, 6-2, 6-3, 6-4, 6-5, 6-6, 6-7, 6-8, 6-9, 6-10 and 6-11 of the present invention showed the activity level evaluated as A.

Test Example 3

Insecticidal Test on *Plutella xylostella*

Adults of *Plutella xylostella* were released onto Chinese cabbage seedlings and allowed to lay eggs thereon. At 2 days after the release of the adults, the Chinese cabbage seedlings with laid eggs were dipped for about 30 seconds in agrochemical dispersions diluted to 500 ppm, each of which contained a different kind of oxime group-containing quinoline compound represented by the general formula (1) of the present invention as an active ingredient. After air-dried, the seedlings were kept in a thermostatic chamber at 25° C. At 6 days after the dip treatment, the number of hatched larvae per plot was counted, the mortality rate was calculated according to the formula shown below, and the insecticidal efficacy was evaluated according to the criteria of Test Example 2. This test was conducted in triplicate using 10 adults of *Plutella xylostella* per plot.

Corrected mortality rate (%)=100×(Number of hatched larvae in a non-treatment plot−Number of hatched larvae in a treatment plot)/Number of hatched larvae in a non-treatment plot [Math. 3]

As a result, the compounds 1-1, 1-7, 2-1, 2-2, 2-3, 2-5, 2-7, 2-8, 2-11, 2-13, 2-19, 2-21, 2-22, 2-23, 2-24, 2-25, 2-26, 2-27, 2-28, 2-29, 2-31, 2-32, 2-33, 2-34, 2-35, 2-36, 2-37, 2-38, 2-39, 3-1, 3-2, 3-8, 3-21, 3-23, 3-27, 3-33, 4-21, 4-25, 4-27, 4-39, 4-41, 5-1, 5-2, 5-3, 5-4, 5-5, 5-6, 5-7, 5-8, 6-1, 6-2, 6-3, 6-4, 6-5, 6-6, 6-7, 6-8, 6-9, 6-10 and 6-11 of the present invention showed the activity level evaluated as A.

INDUSTRIAL APPLICABILITY

The compound of the present invention is highly effective for the control of a wide range of agricultural and horticultural pests and thus is useful.

The invention claimed is:
1. An oxime group-containing quinoline compound represented by the general formula (1):

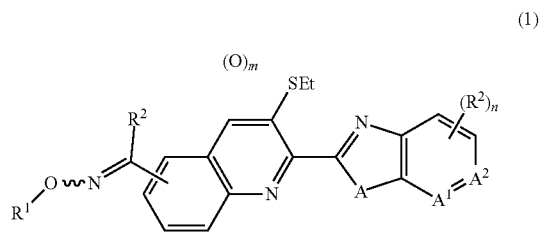

wherein
$R^1$ represents:
(a1) a hydrogen atom;
(a2) a ($C_1$-$C_6$) alkyl group;
(a3) a ($C_2$-$C_6$) alkenyl group;
(a4) a ($C_2$-$C_6$) alkynyl group;
(a5) a ($C_3$-$C_6$) cycloalkyl group;
(a6) a ($C_3$-$C_6$) cycloalkyl ($C_1$-$C_6$) alkyl group;
(a7) a ($C_1$-$C_6$) alkoxy ($C_1$-$C_6$) alkyl group;
(a8) a halo ($C_1$-$C_6$) alkyl group;
(a9) a halo ($C_2$-$C_6$) alkenyl group;
(a10) a halo ($C_2$-$C_6$) alkynyl group;
(a11) a ($C_1$-$C_6$) alkylthio ($C_1$-$C_6$) alkyl group;
(a12) a phenyl ($C_1$-$C_6$) alkyl group;
(a13) a phenyl ($C_1$-$C_6$) alkyl group having, on the ring, 1 to 5 substituting groups which may be the same or different and are selected from (a) a halogen atom, (b) a cyano group, (c) a nitro group, (d) a formyl group, (e) a ($C_1$-$C_6$) alkyl group, (f) a halo ($C_1$-$C_6$) alkyl group, (g) a ($C_1$-$C_6$) alkoxy group, (h) a halo ($C_1$-$C_6$) alkoxy group, (i) a ($C_3$-$C_6$) cycloalkyl ($C_1$-$C_6$) alkoxy group, (j) a ($C_1$-$C_6$) alkylthio group, (k) a halo ($C_1$-$C_6$) alkylthio group, (l) a ($C_1$-$C_6$) alkylsulfinyl group, (m) a halo ($C_1$-$C_6$) alkylsulfinyl group, (n) a ($C_1$-$C_6$) alkylsulfonyl group or (o) a halo ($C_1$-$C_6$) alkylsulfonyl group;
(a14) a ($C_1$-$C_6$) alkylsulfinyl ($C_1$-$C_6$) alkyl group;
(a15) a ($C_1$-$C_6$) alkylsulfonyl ($C_1$-$C_6$) alkyl group;
(a16) a ($C_1$-$C_6$) alkylcarbonyl group;
(a17) a ($C_1$-$C_6$) alkoxycarbonyl group;
(a18) a halo ($C_1$-$C_6$) alkylthio ($C_1$-$C_6$) alkyl group; or
(a19) a ($C_1$-$C_6$) alkyl (N≡CN═)S($C_1$-$C_6$) alkyl group,
$R^2$ represents:
(b1) a hydrogen atom;
(b2) a ($C_1$-$C_6$) alkyl group;
(b3) a cyano group; or
(b4) a ($C_3$-$C_6$) cycloalkyl group,
$R^3$ represents:
(c1) a halogen atom;
(c2) a cyano group;
(c3) a nitro group;
(c4) a ($C_1$-$C_6$) alkyl group;
(c5) a ($C_1$-$C_6$) alkoxy group;
(c6) a ($C_2$-$C_6$) alkenyloxy group;
(c7) a ($C_2$-$C_6$) alkynyloxy group;
(c8) a halo ($C_1$-$C_6$) alkyl group;
(c9) a halo ($C_1$-$C_6$) alkoxy group;
(c10) a halo ($C_2$-$C_6$) alkenyloxy group;
(c11) a halo ($C_2$-$C_6$) alkynyloxy group;
(c12) a ($C_1$-$C_6$) alkylthio group;
(c13) a ($C_1$-$C_6$) alkylsulfinyl group;
(c14) a ($C_1$-$C_6$) alkylsulfonyl group;
(c15) a halo ($C_1$-$C_6$) alkylthio group;
(c16) a halo ($C_1$-$C_6$) alkylsulfinyl group; or
(c17) a halo ($C_1$-$C_6$) alkylsulfonyl group,
A represents an oxygen atom or N—$R^4$ (wherein $R^4$ represents a hydrogen atom or a ($C_1$-$C_6$) alkyl group), A¹ and A² may be the same or different, and each represent CH, a nitrogen atom or an N-oxide,
m represents 0, 1 or 2, and
n represents 0, 1 or 2,
or a salt thereof.

2. The oxime group-containing quinoline compound or the salt according to claim 1, wherein
$R^1$ represents:
(a1) a hydrogen atom;
(a2) a ($C_1$-$C_6$) alkyl group;
(a6) a ($C_3$-$C_6$) cycloalkyl ($C_1$-$C_6$) alkyl group;
(a7) a ($C_1$-$C_6$) alkoxy ($C_1$-$C_6$) alkyl group;
(a8) a halo ($C_1$-$C_6$) alkyl group;
(a11) a ($C_1$-$C_6$) alkylthio ($C_1$-$C_6$) alkyl group;
(a14) a ($C_1$-$C_6$) alkylsulfinyl ($C_1$-$C_6$) alkyl group;
(a15) a ($C_1$-$C_6$) alkylsulfonyl ($C_1$-$C_6$) alkyl group;
(a16) a ($C_1$-$C_6$) alkylcarbonyl group;
(a17) a ($C_1$-$C_6$) alkoxycarbonyl group;
(a18) a halo ($C_1$-$C_6$) alkylthio ($C_1$-$C_6$) alkyl group; or
(a19) a ($C_1$-$C_6$) alkyl (N≡CN═)S($C_1$-$C_6$) alkyl group,
$R^2$ represents:
(b1) a hydrogen atom;
(b2) a ($C_1$-$C_6$) alkyl group; or
(b3) a cyano group,
$R^3$ represents:
(c8) a halo ($C_1$-$C_6$) alkyl group;
(c15) a halo ($C_1$-$C_6$) alkylthio group; or
(c17) a halo ($C_1$-$C_6$) alkylsulfonyl group,
A represents an oxygen atom or N—$R^4$ (wherein $R^4$ represents a ($C_1$-$C_6$) alkyl group),
A¹ and A² each represent CH or a nitrogen atom,
m represents 2, and
n represents 1.

3. The oxime group-containing quinoline compound or the salt according to claim 1, wherein
$R^1$ represents:
(a1) a hydrogen atom;
(a2) a ($C_1$-$C_6$) alkyl group;
(a6) a ($C_3$-$C_6$) cycloalkyl ($C_1$-$C_6$) alkyl group;
(a7) a ($C_1$-$C_6$) alkoxy ($C_1$-$C_6$) alkyl group;
(a8) a halo ($C_1$-$C_6$) alkyl group;
(a11) a ($C_1$-$C_6$) alkylthio ($C_1$-$C_6$) alkyl group;
(a14) a ($C_1$-$C_6$) alkylsulfinyl ($C_1$-$C_6$) alkyl group;
(a15) a ($C_1$-$C_6$) alkylsulfonyl ($C_1$-$C_6$) alkyl group;
(a16) a ($C_1$-$C_6$) alkylcarbonyl group;
(a17) a ($C_1$-$C_6$) alkoxycarbonyl group;
(a18) a halo ($C_1$-$C_6$) alkylthio ($C_1$-$C_6$) alkyl group; or
(a19) a ($C_1$-$C_6$) alkyl (N≡CN═)S($C_1$-$C_6$) alkyl group,
$R^2$ represents:
(b1) a hydrogen atom; or
(b2) a ($C_1$-$C_6$) alkyl group,
$R^3$ represents:
(c8) a halo ($C_1$-$C_6$) alkyl group;
(c15) a halo ($C_1$-$C_6$) alkylthio group; or
(c17) a halo ($C_1$-$C_6$) alkylsulfonyl group,
A represents an oxygen atom or N—$R^4$ (wherein $R^4$ represents a ($C_1$-$C_6$) alkyl group),
A¹ and A² may be the same or different, and each represent CH or a nitrogen atom,
m represents 2, and
n represents 1.

4. An agricultural and horticultural insecticide comprising the oxime group-containing quinoline compound or the salt according to claim 1 as an active ingredient.

5. A method for using an agricultural and horticultural insecticide, comprising treating plants or soil with an effective amount of the oxime group-containing quinoline compound or the salt according to claim 1.

6. An animal ectoparasite control agent comprising the oxime group-containing quinoline compound or the salt according to claim 1 as an active ingredient.

* * * * *

UNITED STATES PATENT AND TRADEMARK OFFICE
CERTIFICATE OF CORRECTION

Page 1 of 2

PATENT NO. : 10,435,411 B2
APPLICATION NO. : 16/346047
DATED : October 8, 2019
INVENTOR(S) : Shimizu et al.

It is certified that error appears in the above-identified patent and that said Letters Patent is hereby corrected as shown below:

On the Title Page

Column 2, Item (56), Line 6, under U.S. Patent Documents, delete "Yonennura" and insert --Yonemura--.

In the Specification

In Column 8, Line 59, delete "t-allylpalladium" and insert --π-allylpalladium--.

In Column 16, Line 55, delete "iwasakii" and insert --iwasaki--.

In Column 16, Line 59, delete "Rhopalosophum" and insert --Rhopalosiphum--.

In Column 17, Line 3, delete "longispinis" and insert --longispinus--.

In Column 17, Line 11, delete "Uroeucon" and insert --Uroleucon--.

In Column 17, Line 16, delete "spinolai" and insert --spinolae--.

In Column 17, Line 23, delete "Rhopalosophum" and insert --Rhopalosiphum--.

In Column 17, Line 32, delete "vitifolii" and insert --vitifoli--.

In Column 18, Line 39, before "Arge pagana," delete "infumata,".

In Column 18, Line 57, delete "FrankLinella" and insert --Frankliniella--.

In Column 19, Line 1, delete "sylvairum" and insert --sylviarum--.

In Column 19, Line 5, delete "Octodectes" and insert --Otodectes--.

Signed and Sealed this
Thirty-first Day of March, 2020

Andrei Iancu
*Director of the United States Patent and Trademark Office*

CERTIFICATE OF CORRECTION (continued)
U.S. Pat. No. 10,435,411 B2

In Column 19, Line 6, delete "ptrenyssnus" and insert --pteronyssinus--.

In Column 19, Line 9, delete "Rhyzoglyphus" and insert --Rhizoglyphus--.

In Column 19, Line 29, delete "Tylenchus" and insert --Tylenchulus--.

In Column 19, Line 33, delete "Lehmannina" and insert --Lehmannia--.

In Column 19, Line 47, delete "taiwanesis" and insert --taiwanensis--.

In Column 20, Line 3, delete "Dalmalinia" and insert --Damalinia--.

In Column 20, Line 14 (Approx.), after "Multiceps" delete "multiceps".

In Column 21, Line 47, delete "6-endotoxins" and insert --$\delta$-endotoxins--.

In Column 21, Lines 65-66, delete "6-endotoxin" and insert --$\delta$-endotoxin--.

In Column 27, Line 2, delete "isoamidofos isoxathion" and insert --isoamidofos, isoxathion--.

In Column 27, Line 50, delete "flurimfen" and insert --flurofen--.

In Column 28, Line 42, delete "benzensulfonate" and insert --benzenesulfonate--.

In Column 29, Line 5, delete "benthiazole" and insert --benzothiazole--.

In Column 29, Line 37, delete "imazamethapyr" and insert --imazmethapyr--.

In Column 30, Line 44, delete "flumezin" and insert --fluomizin--.

In Column 32, Line 16, delete "critatus" and insert --cristatus--.

In Column 38, Line 31, delete "Ethylsulfonyl" and insert --ethylsulfonyl--.

In Column 39, Line 15, delete "Ethylsulfonyl" and insert --ethylsulfonyl--.